United States Patent [19]
Yokoyama et al.

[11] Patent Number: 6,080,396
[45] Date of Patent: Jun. 27, 2000

[54] ANTHRACYCLINE COMPOUND DERIVATIVE AND PHARMACEUTICAL PREPARATION CONTAINING THE SAME

[75] Inventors: Masayuki Yokoyama, Matsudo; Kazunori Kataoka, Kashiwa; Teruo Okano, Ichikawa; Yasuhisa Sakurai, 17-6, Eihuku 3-chome, Suginami-ku, Tokyo 168; Shigeto Fukushima, Narashino; Ryuji Uehara, Takasaki; Tomoko Akutsu, Maebashi; Kazuya Okamoto; Hiroko Mashiba, both of Tokyo; Megumi Machida, Fukaya; Kazuhisa Shimizu, Takasaki, all of Japan

[73] Assignees: Japan Science and Technology Corporation, Kawaguchi; Yasuhisa Sakurai; Nippon Kayaku Kabushiki Kaisha, both of Tokyo, all of Japan

[21] Appl. No.: 08/836,965

[22] PCT Filed: Sep. 26, 1996

[86] PCT No.: PCT/JP96/02789

§ 371 Date: Aug. 18, 1997

§ 102(e) Date: Aug. 18, 1997

[87] PCT Pub. No.: WO97/12895

PCT Pub. Date: Apr. 10, 1997

[30] Foreign Application Priority Data

Sep. 29, 1995 [JP] Japan .................................... 7-253404

[51] Int. Cl.$^7$ .......................... A61K 9/127; A61K 31/70; C07M 17/08
[52] U.S. Cl. .................... 424/78.08; 424/78.17; 424/450; 424/451; 424/489; 424/501; 514/34; 536/6.4
[58] Field of Search .................. 514/35, 34; 536/6.5; 424/78.08, 78.17, 450, 451, 489, 501

[56] References Cited

U.S. PATENT DOCUMENTS

| | | | |
|---|---|---|---|
| 4,263,428 | 4/1981 | Apple et al. | 536/6.4 |
| 4,625,019 | 11/1986 | Relyveld | 536/6.4 |
| 5,412,072 | 5/1995 | Sakurai et al. | 530/322 |
| 5,449,513 | 9/1995 | Yokoyama et al. | 424/78.08 |
| 5,510,103 | 4/1996 | Yokoyama et al. | 424/78.08 |

FOREIGN PATENT DOCUMENTS

| | | |
|---|---|---|
| 0 004 467 | 10/1979 | European Pat. Off. . |
| 0 721 776 | 1/1996 | European Pat. Off. . |
| 2-300133 | 12/1990 | Japan . |
| 3-287545 | 12/1991 | Japan . |
| 5-955 | 1/1993 | Japan . |
| 5-117385 | 5/1993 | Japan . |
| 5-124969 | 5/1993 | Japan . |
| 6-107565 | 4/1994 | Japan . |
| 6-206815 | 7/1994 | Japan . |
| 6-206830 | 7/1994 | Japan . |
| 7-69900 | 3/1995 | Japan . |
| 8-188541 | 7/1996 | Japan . |

*Primary Examiner*—Elli Peselev
*Attorney, Agent, or Firm*—Nields, Lemack & Dingman

[57] ABSTRACT

A dimer, trimer or tetramer of an anthracycline compound which can be obtained by directly, chemically bonding anthracycline compounds having anticancer activities to each other by an alkali treatment. A high molecular block copolymer-drug complex pharmaceutical preparation in which the high molecular block copolymer having a hydrophilic polymer segment and a hydrophobic polymer segment forms a micelle having the hydrophilic segment as its outer shell and contains in its hydrophobic inner core a dimer, trimer or tetramer of anthracycline compound alone or together with other drugs. A high molecular block copolymer-drug complex pharmaceutical preparation in which the high molecular block copolymer having a hydrophilic polymer segment and a hydrophobic polymer segment forms a micelle having the hydrophilic segment as its outer shell and contains in its hydrophobic inner core an anthracycline anticancer agent, wherein, when the pharmaceutical preparation is intravenously administered to a CDF1 mouse, the amount of the anthracycline anticancer agent in 1 ml of the mouse blood plasma after 1 hour of its administration becomes 10 (% of dose/ml) or more, provided that the amount of anthracycline anticancer agent in the administered preparation is defined as 100. The aforementioned pharmaceutical preparations have high drug effects and low toxicities.

16 Claims, 27 Drawing Sheets

ANTHRACYCLINE COMPOUND DERIVATIVE AND PHARMACEUTICAL PREPARATION CONTAINING THE SAME

TECHNICAL FIELD

This invention relates to a novel anthracycline compound derivative and a high molecular block copolymer-drug complex pharmaceutical preparation which contains the derivative.

BACKGROUND ART

Daunomycin (British Patent 1003383, U.S. Pat. No. 3,616,242), adriamycin (U.S. Pat. No. 3,590,028, U.S. Pat. No. 3,803,124) and the like obtained from culture liquids of actinomycetes are known as anthracycline anticancer agents. They have broad anticancer spectrums against experimental tumors and also are clinically used widely as cancer chemotherapeutics. On the contrary, however, it is known that they frequently cause serious side effects, such as leukopenia, alopecia, myocardial disorder and the like.

In order to resolve this problem, various derivatives have been proposed. For example, pirarubicin (common name) aims at reducing its toxicity by introducing a tetrahydropyranyl group into the 4' position of the sugar moiety of adriamycin.

Also, epirubicin (common name) is a compound in which a hydroxyl group on the 4' position of the sugar moiety of adriamycin is bound to the a position, thereby attempting to reduce its toxicity.

However, though these drugs have lower toxicities in comparison with adriamycin, their problems such as limited total doses and the like are not completely settled yet.

On the other hand, it is a well known technique to make use of a high molecular micelle formed from a block copolymer to improve solubility of drugs which are slightly soluble in water. And it has been confirmed that high molecular block copolymer-drug complex pharmaceutical preparations obtained in Japanese Patent Application (Kokai) No. 2-300133, Japanese Patent Application (Kokai) No. 6-107565, Japanese Patent Application (Kokai) No. 5-955, Japanese Patent Application (Kokai) No. 5-124969, Japanese Patent Application (Kokai) No. 5-117385, Japanese Patent Application (Kokai) No. 6-206830, Japanese Patent Application (Kokai) No. 7-69900 and Japanese Patent Application (Kokai) No. 6-206815 are possessed of anticancer effects which are superior to those of adriamycin.

DISCLOSURE OF THE INVENTION

The inventors of the present invention have conducted intensive studies on a high molecular block copolymer-drug complex pharmaceutical preparation which is possessed of both higher effect and lower toxicity in comparison with the prior art high molecular block copolymer-drug complex pharmaceutical preparations, and have accomplished the present invention as a result of the efforts.

Accordingly, the present invention relates to:

(1) a dimer, trimer or tetramer of anthracycline compound which can be obtained by directly, chemically bonding anthracycline compound or compounds having anticancer activities to each other by an alkali treatment;

(2) the dimer, trimer or tetramer of anthracycline compound according to the aforementioned item (1) wherein the anthracycline compound or compounds comprise at least one kind of compound selected from adriamycin, daunomycin, pirarubicin, epirubicin and acid salts thereof;

(3) a dimer of anthracycline compound which can be obtained by directly, chemically bonding adriamycin molecules or acid salts thereof to each other, or by directly, chemically bonding adriamycin or an acid salt thereof to daunomycin or an acid salt thereof, by an alkali treatment;

(4) the dimer, trimer or tetramer of anthracycline compound according to the aforementioned item (1), (2) or (3) wherein the mutual binding mode of anthracycline compounds is Schiff base bonding;

(5) the dimer of adriamycin having the structure of the following formula (AA):

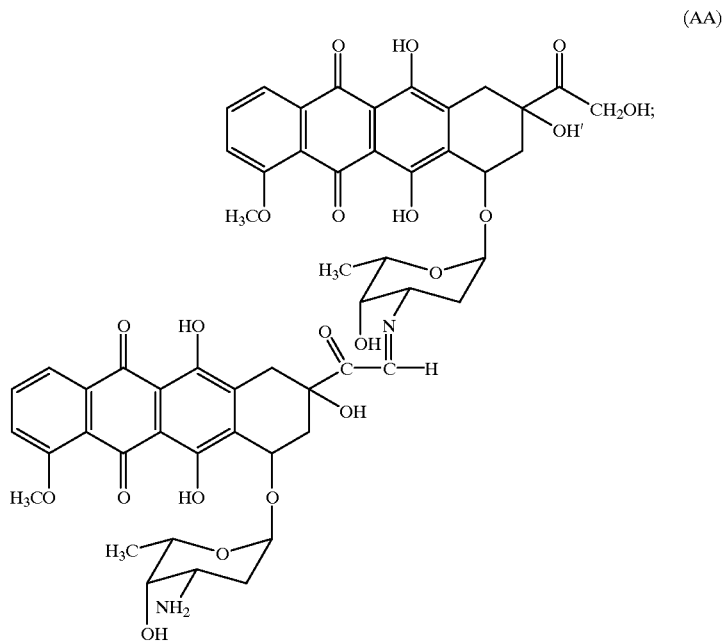

(AA)

(6) a trimer of adriamycin which can be obtained by directly, chemically bonding adriamycin molecules or acid salts thereof to each other by an alkali treatment and has the mass spectrum shown in FIG. 7;

(7) a high molecular block copolymer-drug complex pharmaceutical preparation in which the high molecular block copolymer having a hydrophilic polymer segment and a hydrophobic polymer segment forms a micelle having the hydrophilic segment as its outer shell and contains in its hydrophobic inner core a dimer, trimer or tetramer of anthracycline compound, if necessary together with other drugs;

(8) the high molecular block copolymer-drug complex pharmaceutical preparation according to the aforementioned item (7) wherein the dimer, trimer or tetramer of anthracycline compound is the dimer, trimer or tetramer of anthracycline compound of the aforementioned item (1), (2), (3), (4), (5) or (6);

(9) the high molecular block copolymer-drug complex pharmaceutical preparation according to the aforementioned item (7) or (8) wherein the high molecular block copolymer has a structure of the following formula (1) or (2):

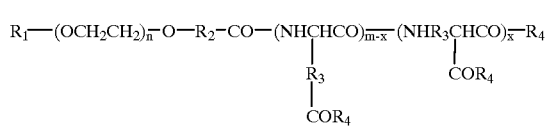

(1)

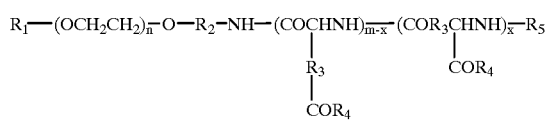

(2)

wherein $R_1$ represents a hydrogen atom or a lower alkyl group, $R_2$ represents a binding group, $R_3$ represents a methylene or ethylene group, $R_4$ independently represents a hydroxyl group or a residue of an anthracycline compound having anticancer activity, $R_5$ represents a hydrogen atom or a protecting group, n is an integer of 5 to 1,000, m is an integer of 2 to 300 and x is an integer of 0 to 300, with the proviso that x is not larger than m;

(10) the high molecular block copolymer-drug complex pharmaceutical preparation according to the aforementioned item (9) wherein the residue of the anthracycline compound having anticancer activity is a group represented by the following formula (3):

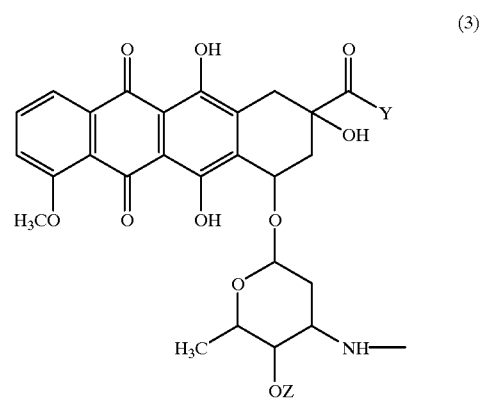

(3)

wherein Y represents —$CH_2OH$ or —$CH_3$ and Z represents H or

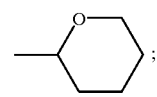

;

(11) the high molecular block copolymer-drug complex pharmaceutical preparation according to the aforementioned item (7), (8), (9) or (10) wherein it contains in the inner core of micelle formed by the high molecular block copolymer a dimer, trimer or tetramer of anthracycline compound in an amount of from 2 to 60% by weight based on the high molecular block copolymer;

(12) the high molecular block copolymer-drug complex pharmaceutical preparation according to the aforementioned item (7), (8), (9), (10) or (11) wherein the dimer, trimer or tetramer of anthracycline compound is the dimer of adriamycin;

(13) the high molecular block copolymer-drug complex pharmaceutical preparation according to the aforementioned item (7), (8), (9), (10), (11) or (12) wherein it contains in the inner core of micelle formed by the high molecular block copolymer the anthracycline anticancer agent and the dimer, trimer or tetramer of anthracycline compound at the ratio of 1:0.5~20 by weight;

(14) the high molecular block copolymer-drug complex pharmaceutical preparation according to the aforementioned item (13) wherein the anthracycline anticancer agent and the dimer, trimer or tetramer of anthracycline compound are contained at the ratio of 1:0.7~10 by weight;

(15) the high molecular block copolymer-drug complex pharmaceutical preparation according to the aforementioned item (13) wherein the anthracycline anticancer agent and the dimer, trimer or tetramer of anthracycline compound are contained at the ratio of 1:1~5 by weight;

(16) the high molecular block copolymer-drug complex pharmaceutical preparation according to the aforementioned item (13), (14) or (15) wherein the anthracycline anticancer agent is at least one agent selected from adriamycin, daunomycin, pirarubicin, epirubicin and acid salts thereof;

(17) a high molecular block copolymer-drug complex pharmaceutical preparation in which the high molecular block copolymer having a hydrophilic polymer segment and a hydrophobic polymer segment forms a micelle having the hydrophilic segment as its outer shell and contains in its hydrophobic inner core an anthracycline anticancer agent, wherein, when the pharmaceutical preparation is intravenously administered to a CDF1 mouse of 7 to 9 week's age, the amount of the anthracycline anticancer agent in 1 ml of the mouse blood plasma after 1 hour of its administration becomes 10 (% of dose/ml) or more, provided that the amount of anthracycline anticancer agent in the administered preparation is defined as 100;

(18) the pharmaceutical preparation according to the aforementioned item (17) wherein the amount of anthracycline anticancer agent in 1 ml of the mouse blood plasma after 1 hour of its administration becomes 20 to 60 (% of dose/ml);

(19) the pharmaceutical preparation according to the aforementioned item (17) or (18) wherein the anthracycline anticancer agent is at least one agent selected from adriamycin, daunomycin, pirarubicin, epirubicin and acid salts thereof; and

(20) the pharmaceutical preparation according to any one of the aforementioned items (7) to (19) wherein it is used for the treatment of a solid cancer.

BEST MODE OF CARRYING OUT THE INVENTION

Figure 1:
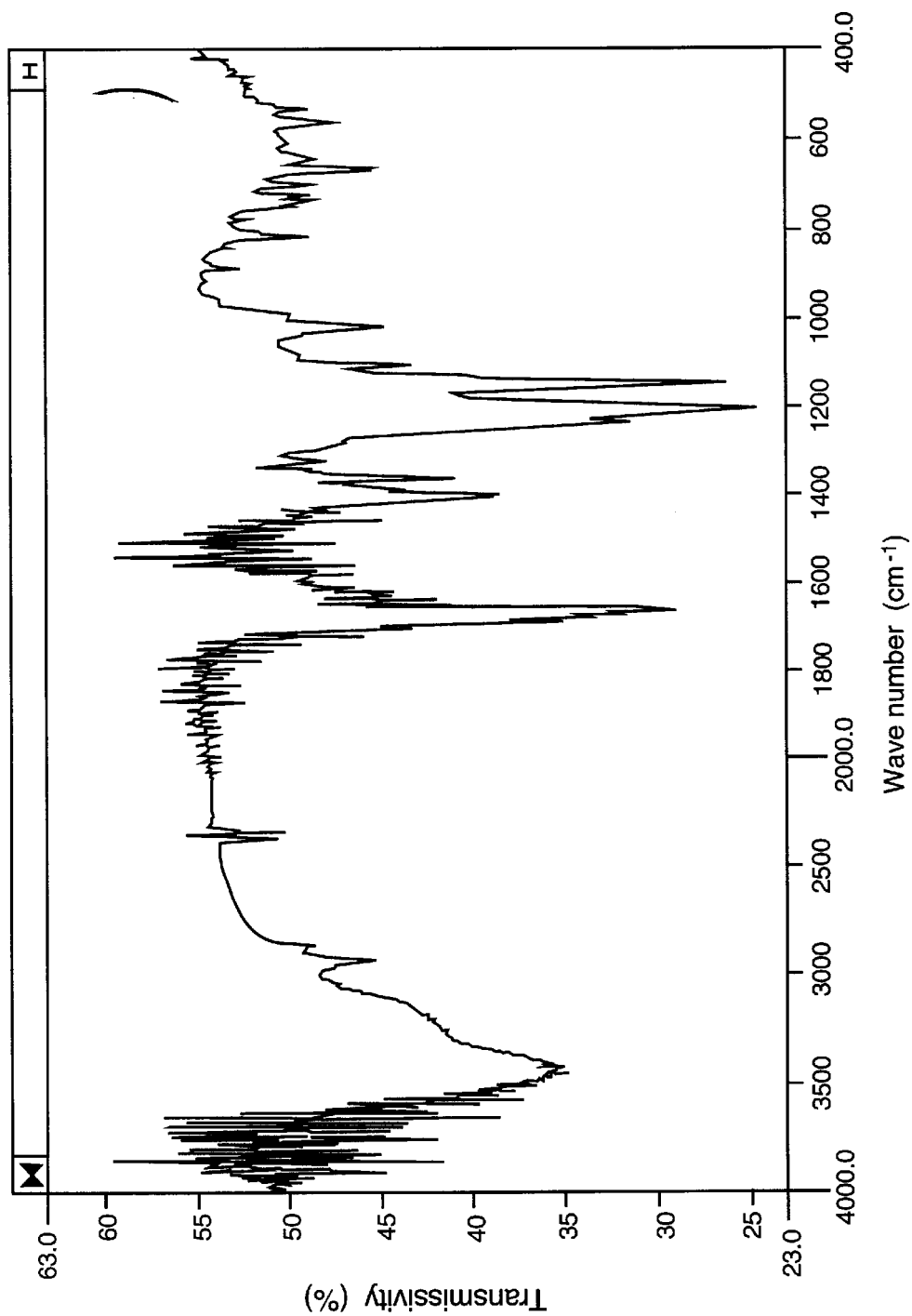
FIG. 1 shows a graph of infrared absorption spectrum of the dimer of adriamycin.

The following describes the present invention in detail.

According to the present invention, it is able to obtain pharmaceutical preparations which have higher effect and lower toxicity in comparison with conventional anthracycline anticancer agents or high molecular block copolymer-drug complex pharmaceutical preparations of the prior art.

Examples of the anthracycline compound having an anticancer activity to be used in the present invention include adriamycin, daunomycin, pirarubicin, epirubicin and acid salts thereof.

The method for preparing the dimer, trimer or tetramer of anthracycline compound of the present invention is not particularly limited, and the said dimer, trimer or tetramer can be obtained, for example, by subjecting an anthracycline compound having an anticancer activity to an alkali treatment. By the alkali treatment, the dimer, trimer or tetramer of the anthracycline compound is obtained through mutual direct chemical bonding (that is, not by a chemical bonding via a cross-linking agent but by a bonding formed from a reaction between functional groups of the anthracycline compounds).

The dimer, trimer or tetramer of anthracycline compound may be obtained by bonding molecules of the same compound or different compounds.

As the alkali treatment, a method in which an anthracycline compound is dissolved in a solvent and a base is added thereto can be exemplified. The solvent to be used is not particularly limited, provided that it can dissolve said compound, and its examples include water, N,N-dimethylformamide (DMF), dimethyl sulfoxide (DMSO), dioxane, tetrahydrofuran (THF), methanol, acetonitrile and a mixture solvent thereof.

As the base to be added, any one of inorganic bases, organic bases and salts thereof can be used with no particular limitation, with the proviso that it is soluble in said solvent and that the solution after addition of the base shows a pH value of exceeding 7 and up to 14. The base concentration is also not particularly limited. Examples of the desirable bases include sodium hydroxide, potassium hydroxide, sodium carbonate, sodium hydrogencarbonate, potassium carbonate, potassium hydrogencarbonate, sodium phosphate, disodium hydrogenphosphate, sodium dihydrogenphosphate, potassium phosphate, dipotassium hydrogenphosphate, potassium dihydrogenphosphate, secondary and tertiary amines having 2 to 20 carbon atoms, and an acid salt adduct thereof. The pH value in the alkali treatment is exceeding 7 and up to 14, and preferably 8 to 10.

The alkali treatment temperature is not particularly limited, provided that the solution does not freeze or boil, and it is preferably 0 to 50° C., more preferably 0 to 40° C. The treatment time is 1 minute to 120 hours, preferably 10 minutes to 24 hours.

The thus obtained dimer, trimer or tetramer of anthracycline compound can be purified by employing a known purification technique. For example, a solid substance may be obtained by freeze-drying, precipitation or the like, or by exchanging the solvent by dialysis or ultrafiltration followed by freeze-drying, precipitation or the like. When further purification of the thus obtained solid substance is required, thin layer chromatography, liquid chromatography or the like can be used.

When a compound having both a substituent of carbonyl structure and an amino group is used as the anthracycline compound, or a compound having a substituent of carbonyl structure is used in combination with another compound having an amino group, a dimer, trimer or tetramer in which the anthracycline compounds are chemically bound to each other via Schiff base bonding is obtained by the aforementioned alkali treatment. In consequence, it is desirable to use as the anthracycline compound a compound having both a substituent of carbonyl structure and an amino group or a compound having a substituent of carbonyl structure in combination with a compound having an amino group. In this connection, examples of the substituent having carbonyl structure include an acyl group having 2 to 5 carbon atoms which may be substituted with a hydroxyl group or a halogen atom, such as fluorine, chlorine, bromine and iodine atom or the like; or an acylalkyl group having 3 to 10 carbon atoms which may be substituted with a hydroxyl group, a halogen atom or the like.

When the dimer, trimer or tetramer in which the anthracycline compound are mutually bound via Schiff base bonding is treated with an acid, at least the anthracycline compound which has been used as a raw material is generated. As the acid treatment, a method in which the dimer, trimer or tetramer of anthracycline compound is dissolved in a solvent and an acid is added thereto can be exemplified. The solvent to be used is not particularly limited, provided that it can dissolve said compound, and its examples include water, N,N-dimethylformamide (DMF), dimethyl sulfoxide (DMSO), dioxane, tetrahydrofuran (THF), methanol, acetonitrile and a mixture solvent thereof. As the acid to be added, any one of inorganic acids, such as hydrochloric, nitric, sulfuric and phosphoric acid, and organic acids, such as formic, acetic and trifluoroacetic acid, can be used.

The pH value in the acid treatment is preferably from 2 to 4, and the treating temperature is not particularly limited, provided that the solution does not freeze or boil, and is preferably from 0 to 50° C., more preferably from 20 to 40° C. The treatment time is within the range of from 1 minute to 120 hours, preferably from 24 to 72 hours.

Figure 2:
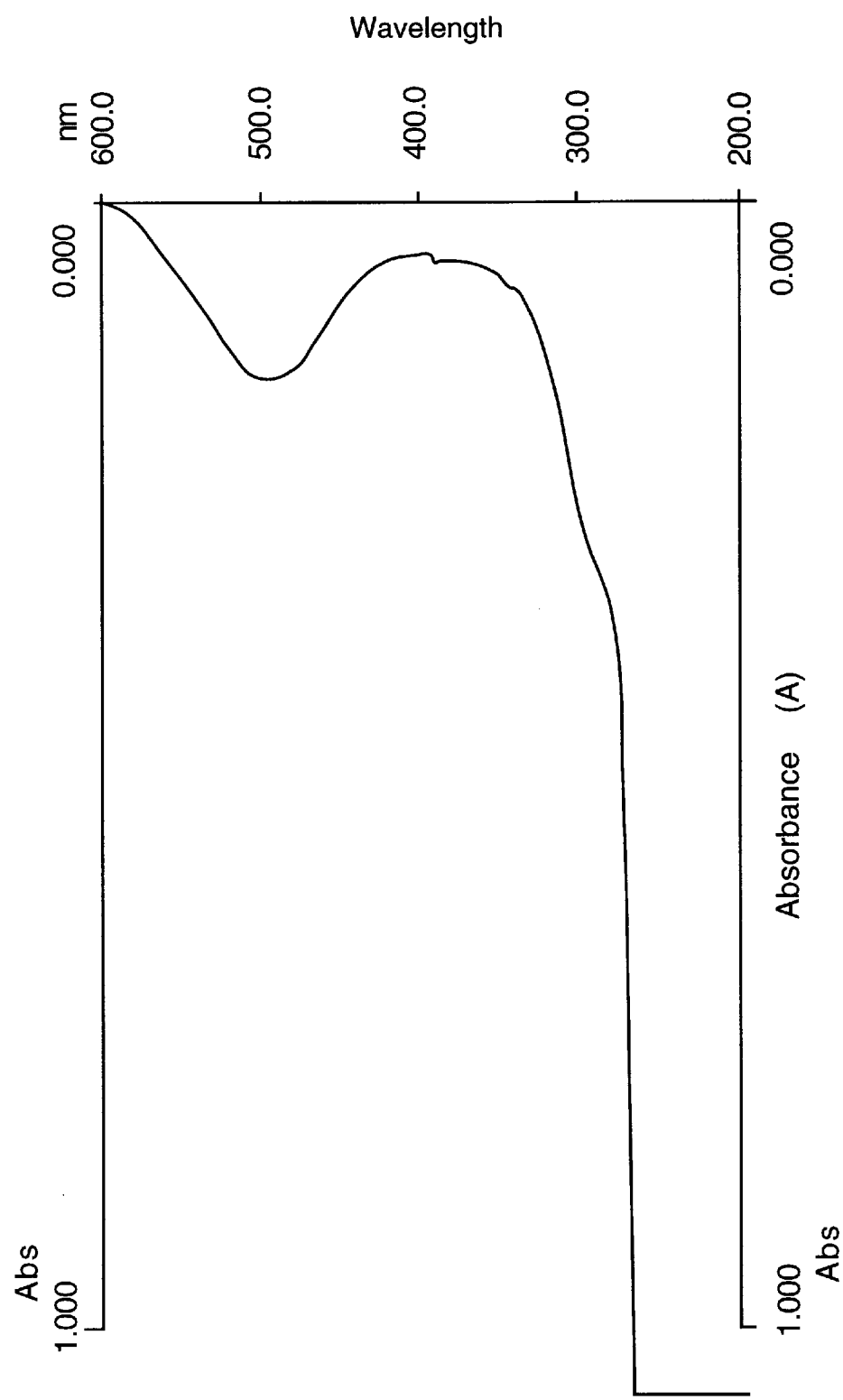
FIG. 2 shows a graph of ultraviolet spectrum of the dimer of adriamycin.
Figure 3:
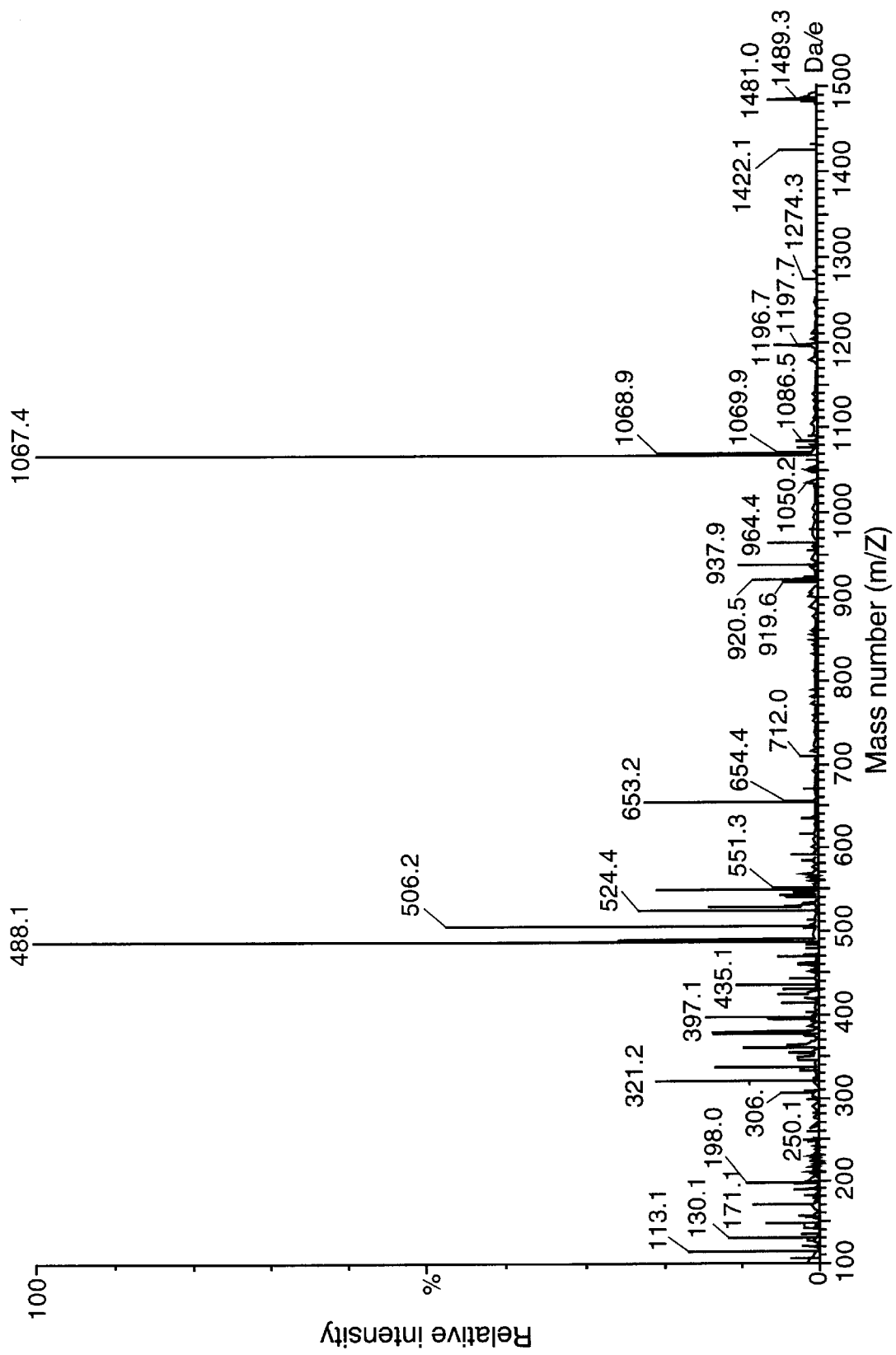
FIG. 3 shows a graph of mass spectrum of the dimer of adriamycin.

As an example of the dimer, trimer or tetramer of anthracycline compound of the present invention which can be obtained through directly, chemically bonding anthracycline compounds by the aforementioned alkali treatment, the dimer of adriamycin having the infrared absorption spectrum shown in FIG. 1 and the ultraviolet spectrum shown in FIG. 2 can be exemplified. This adriamycin dimer also has the mass spectrum shown in FIG. 3. This adriamycin dimer has the structure represented by the aforementioned formula (AA).

Infrared absorption spectrum: 1676, 1417, 1217, 1158 $cm^{-1}$;

Ultraviolet spectrum: λ mas=486 nm;

Mass spectrum (ESI), m/z (%): 1067 (100), 964 (10), 938 (15), 921 (13), 653 (20), 524 (20), 506 (50), 488 (98).

In this connection, the instruments and measuring conditions used for the measurement of these spectra are as follows. The infrared absorption spectrum was measured by the KBr tablet method using System 2000 manufactured by Perkin-Elmer Co. The ultraviolet spectrum was measured in methanol solution using U 3200 Spectrophotometer manufactured by Hitachi Co. The mass spectrum was measured by the electrospray method using QUATTRO 2 Mass Spectrometer manufactured by VG Co.

When treated with the acid, this adriamycin dimer generates adriamycin, together with a compound presumably having a structure represented by the following formula (4):

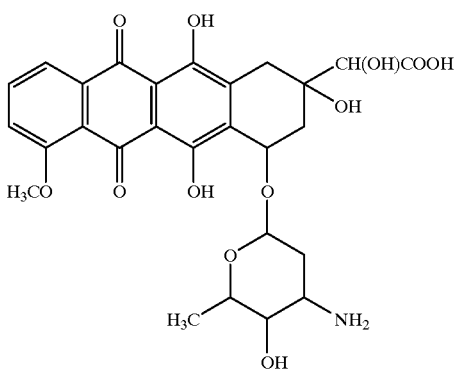

(4)

Figure 4:
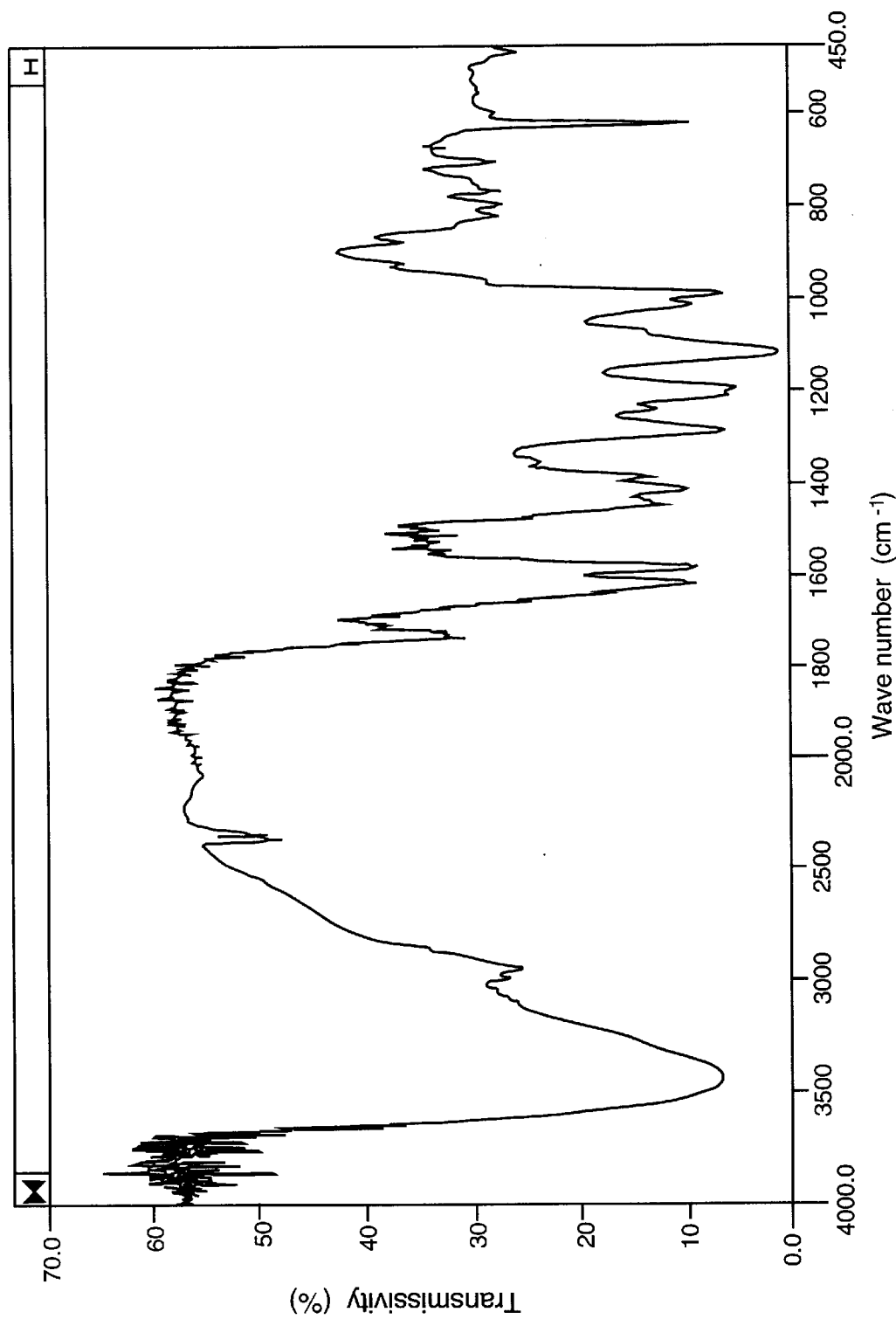
FIG. 4 shows a graph of infrared absorption spectrum of the compound presumably having the structure of formula (4), which is generated together with adriamycin when the dimer of adriamycin is treated with an acid.
Figure 5:
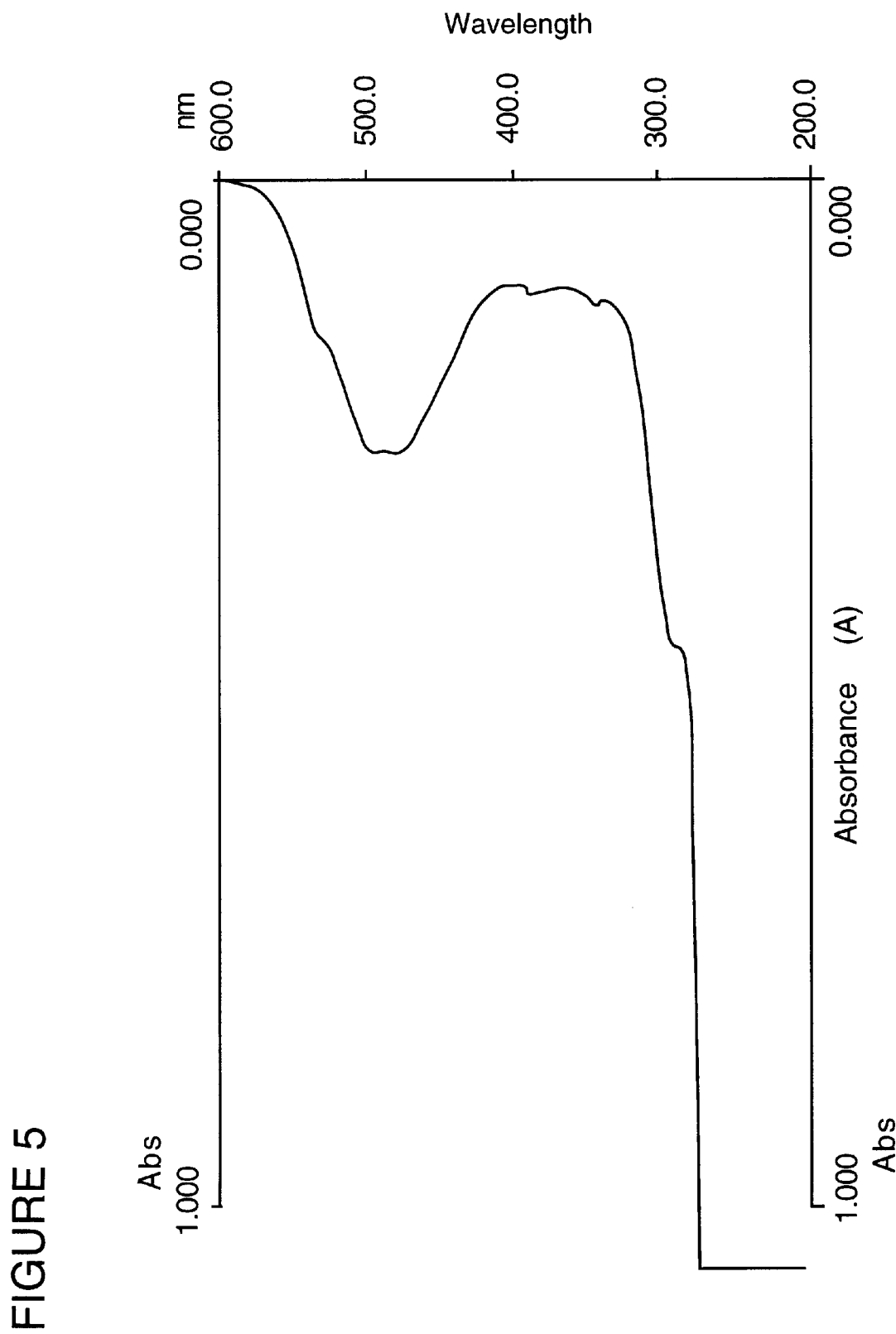
FIG. 5 shows a graph of ultraviolet spectrum of the compound presumably having the structure of formula (4), which is generated together with adriamycin when the dimer of adriamycin is treated with an acid.
Figure 6:
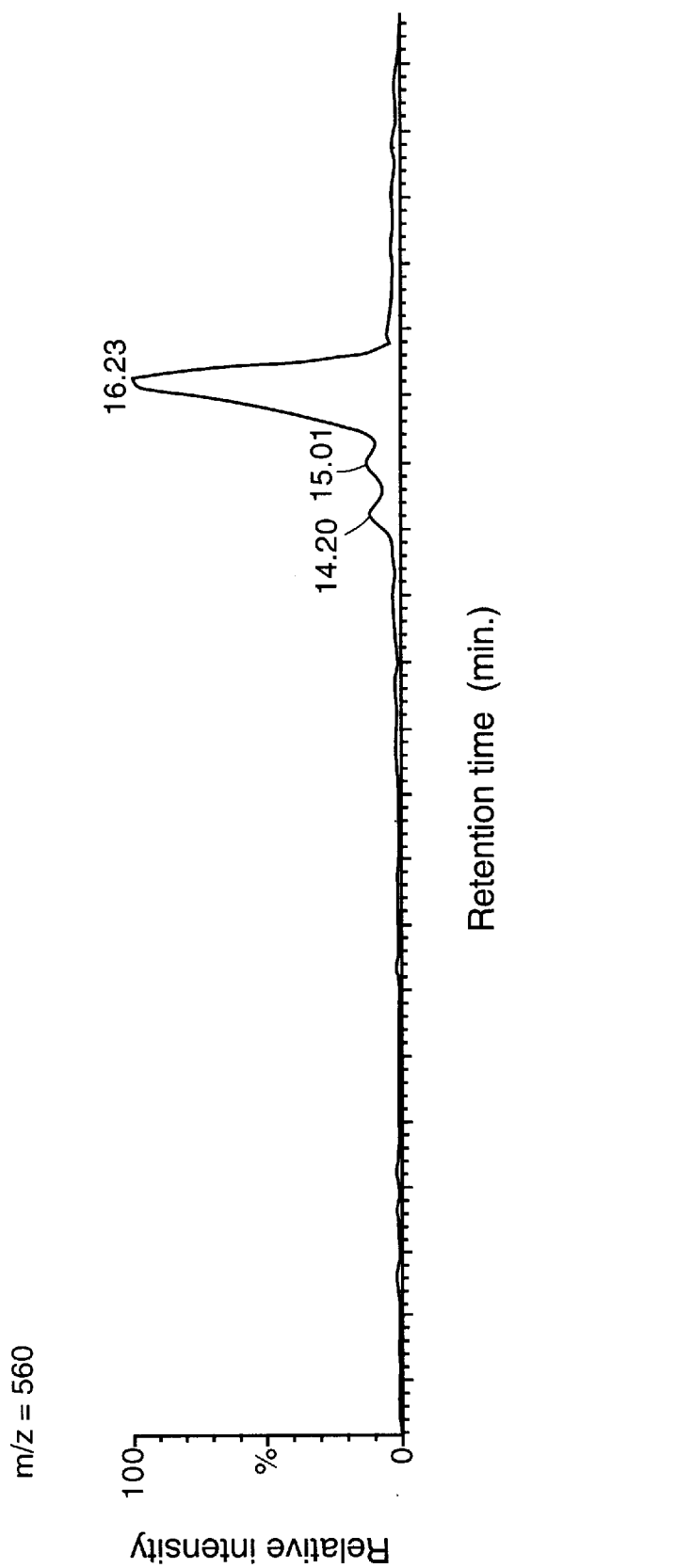
FIG. 6 shows a graph of mass chromatogram (m/z=560) of the compound presumably having the structure of formula (4), which is generated together with adriamycin when the dimer of adriamycin is treated with an acid.

The infrared absorption spectrum, ultraviolet spectrum or mass chromatogram at m/z=560 by LC/MS of the compound presumably having the structure of formula (4) is shown in FIG. 4, FIG. 5 or FIG. 6, respectively.

In this connection, instruments and measuring conditions used for the measurement of these spectra and chromatogram are as follows. The infrared absorption spectrum was measured using the same instrument under the same conditions as those used in the measurement of the spectrum of FIG. 1. The ultraviolet spectrum was measured in benzyl alcohol solution using U 3200 manufactured by Hitachi Co. Instruments and measuring conditions for the measurement of mass chromatogram by LC/MS are as follows. LC:

Column: C4·300 angstrom/5 μm, manufactured by Waters Co.;

Eluent: acetonitrile/0.1% trifluoroacetic acid +0.05% Ms 7 (MS 7; manufactured by Gasukuro Kogyo Co.);

Gradient elution:

| Time (minute) | 0 | 20 | 25 | 30 | 35 | 36 | 40; |
|---|---|---|---|---|---|---|---|
| Acetonitrile concentration (%) | 22 | 40 | 50 | 90 | 90 | 22 | 22; |
| Flow rate: 1 ml/min; | | | | | | | |

MS: QUATTRO 2 (electrospray method) manufactured by VG Co.

Figure 7:
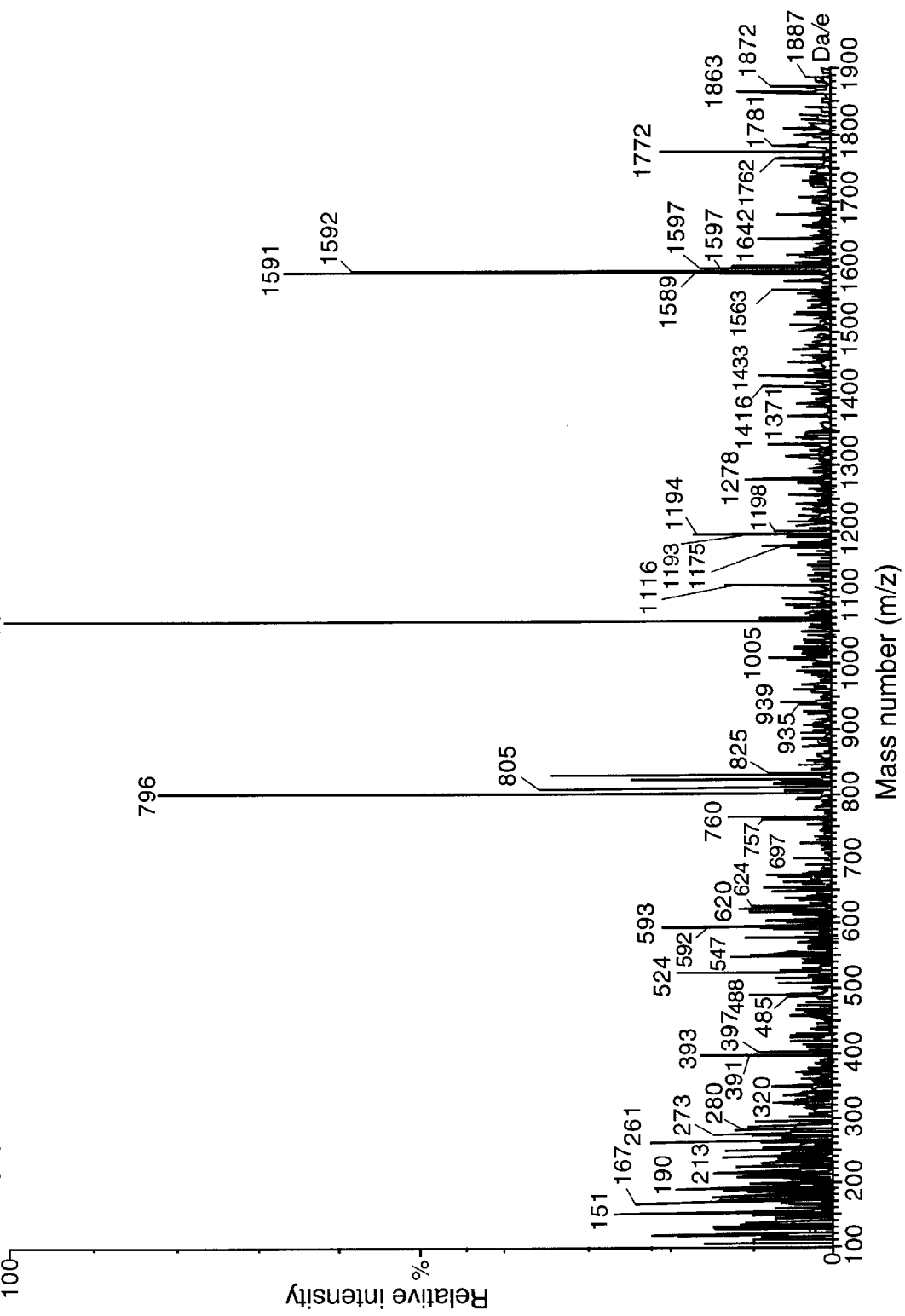
FIG. 7 shows a graph of mass spectrum of the trimer of adriamycin.

As another example of the dimer, trimer or tetramer of anthracycline compound of the present invention which can be obtained through directly, chemically bonding anthracycline compounds by the aforementioned alkali treatment, the trimer of adriamycin, which has the mass spectrum shown in FIG. 7 and generates adriamycin when treated with the acid, can be exemplified.

The structure of the hydrophilic polymer segment of the high molecular block copolymer to be used in the high molecular block copolymer-drug complex pharmaceutical preparation of the present invention can include the structure of polyethylene glycol, polysaccharide, polyacrylamide, polymethacrylamide, polyvinyl alcohol, polyvinyl pyrrolidone, chitosan or the like, though it is not particularly limited thereto with the proviso that it has a hydrophilic polymer structure. The particularly preferred structure is a polyethylene glycol structure.

The structure of the hydrophobic high polymer segment can include the structure of polystyrene, polyamino acids (polyaspartic acid, polyglutamic acid, polylysine and the like), polyacrylic acid, polymethacrylic acid, polymaleic acid, or a derivative thereof or a salt thereof or the like, though it is not particularly limited thereto with the proviso that it has a hydrophobic polymer structure. Of these, a polyamino acid, a derivative thereof or a salt thereof is preferred, and polyaspartic acid, polyglutamic acid, a derivative thereof or a salt thereof is particularly preferred. Though not particularly limited, examples of the salt include a sodium salt, potassium salt and the like.

Examples of the derivatives of polyamino acid structure include those in which hydrophobic compounds such as an aromatic amine, an aliphatic amine, an aromatic alcohol, an aliphatic alcohol, an aromatic thiol, an aliphatic thiol and the like are linked to their side chains, and the hydrophobic groups to be linked to the side chains are not particularly limited with the proviso that they are able to link to the side chains and can make the polyamino acid segment into hydrophobicity. Preferred of these is a polyaspartic or polyglutamic acid derivative in which an amine having an aromatic ring is linked to its side chain.

Preferred examples of the high molecular block copolymer include those which have the aforementioned chemical structure represented by the formula (1) or (2).

In the aforementioned formulae (1) and (2), $R_1$ represents a hydrogen atom or a lower alkyl group, in which lower alkyl groups having 1 to 3 carbon atoms, preferably methyl group, can be exemplified as the lower alkyl group.

The binding group represented by K has a structure which corresponds to the method and compound used in forming the polyamino acid segment at the terminal of the polyethylene glycol segment, in order to convert the terminal of the compound that forms the polyethylene glycol segment into a structure suited for said formation. Its examples include alkylene groups having 1 to 8 carbon atoms, such as a methylene, ethylene, propylene, trimethylene and isobutylene group, of which a trimethylene group is preferred.

$R_3$ represents a methylene or ethylene group, preferably a methylene group.

$R_4$ independently represents a hydroxyl group or a residue of an anthracycline compound having an anticancer activity. As the residue of the anthracycline compound having an anticancer activity, various residues can be used with no particular limitation, and preferably the group represented by the formula (3) can be used. Illustrative examples of the group represented by the formula (3) include the residues of adriamycin, daunomycin, pirarubicin and epirubicin.

Though $R_4$ independently represents a hydroxyl group or the anthracycline compound having an anticancer activity, it is desirable that at least a portion, preferably 5 to 80%, of the total $R_4$ groups present in the high molecular block copolymer are residues of the anthracycline compound having an anticancer activity, more preferably 20 to 60% thereof are said residues of anthracycline compound.

Though $R_4$ independently represents a hydroxyl group or the residue of the anthracycline compound having an anticancer activity, a group having anthracene skeleton or anthraquinone skeleton, such as the substituent having anthracene skeleton or anthraquinone skeleton disclosed in Japanese Patent Application (Kokai) No. 6-206830, may be used in stead of said residue of anthracycline compound.

$R_5$ represents a hydrogen atom or a protecting group, in which an aliphatic or aromatic acyl group can be exemplified as the protecting group. Though not particularly limited, the protecting group can be introduced by a known method such as the method effected by an acid anhydride or the method effected by an acid halide. A hydrogen atom or an acetyl group is desirable as $R_5$.

In addition, n is 5 to 1,000, preferably 15 to 400, m is 2 to 300, preferably 10 to 100, and x is 0 to 300, preferably 0 to 100.

The high molecular block copolymer has a molecular weight of preferably from 1,000 to 100,000, more preferably from 5,000 to 50,000, although the molecular weight is not particularly limited when the block copolymer is soluble in water. The ratio of the hydrophilic polymer segment to the hydrophobic polymer segment in the high molecular block copolymer is not particularly limited, provided that the water solubility of the pharmaceutical preparation of the present invention is maintained, but is preferably 1:0.1~10 (by weight), more preferably 1:0.1~5 (by weight).

Though the drug other than the dimer, trimer or tetramer of anthracycline compound, which may be contained in the inner core of micelle of the high molecular block copolymer, is not necessarily an essential component, its examples include anticancer agents such as adriamycin, daunomycin, pirarubicin, epirubicin, methotrexate, mitomycin C, etoposide, cisplatin and a derivative thereof, of which anthracycline anticancer agents are preferred and adriamycin, daunomycin, pirarubicin, epirubicin or an acid salt thereof is particularly preferred.

The amount of the dimer, trimer or tetramer of anthracycline compound to be contained in the high molecular block copolymer-drug complex pharmaceutical preparation is preferably from 1 to 100% by weight, more preferably from 2 to 60% by weight, based on the high molecular block copolymer. However, the dimer, trimer or tetramer can be used in an amount as large as possible with no problems, provided that it does not spoil the micelle forming ability of the high molecular block copolymer-drug complex pharmaceutical preparation.

The amount of other drug than the dimer, trimer or tetramer of anthracycline compound to be contained in the high molecular block copolymer-drug complex pharmaceutical preparation is preferably from 0 to 100% by weight, more preferably from 2 to 60% by weight, based on the high molecular block copolymer. However, said other drug can be used in an amount as large as possible with no problems, provided that it does not spoil the micelle forming ability of the high molecular block copolymer-drug complex pharmaceutical preparation.

When the high molecular block copolymer-drug complex pharmaceutical preparation contains "other drug than the dimer, trimer or tetramer of anthracycline compound", the ratio of "other drug than the dimer, trimer or tetramer of anthracycline compound" to "the dimer, trimer or tetramer of anthracycline compound" is generally 1:0.05~100 by weight, preferably 1:0.5~20 by weight, more preferably 1:0.7~10 by weight, most preferably 1:1~5 by weight.

Though the dimer, trimer or tetramer of anthracycline compound to be contained in the inner core of micelle of the high molecular block copolymer is not particularly limited, the dimers, trimers or tetramers of the anthracycline compound described in the aforementioned items (1) to (6) are desirable. Only one of these dimers, trimers or tetramers may be contained in the inner core of micelle, or two or more of them may be contained in the inner core of micelle.

The method for the preparation of the high molecular block copolymer is well known, and it can be prepared for example in the following manner. That is, it can be prepared by allowing a compound which will constitute the hydrophilic polymer segment (for example, polyethylene glycol, polysaccharide, polyacrylamide, polymethacrylamide, polyvinyl alcohol, polyvinyl pyrrolidone, chitosan or a derivative thereof) or its terminal-modified product to react with a polymer compound that will constitute the hydrophobic polymer segment, or by allowing a compound which will constitute the hydrophilic polymer segment or its terminal-modified product to react with a polymerizable monomer and then, if necessary, carrying out a chemical reaction such as a derivative formation.

As an example of the derivative formation, when the hydrophobic polymer segment has a polymeric carboxylic acid structure, it may be mentioned to react a hydrophobic compound therewith in order to increase the hydrophobic property. The hydrophobic compound forms an ester bond, amide bond or the like and thereby binds to the high molecular block copolymer. These reactions can be effected by commonly known methods such as esterification, amidation and the like. For example, when a hydrophobic compound is linked by an amide bonding to a high molecular block copolymer having a hydrophilic polymer segment and a polymeric carboxylic acid segment (raw material copolymer), the reaction can be carried out in accordance with a conventional method known as peptide bond formation method. For example, an acid halide method, an acid anhydride method, a coupling method and the like can be used, of which a coupling method in which a condensing agent is used is desirable. With regard to the condensing agent, 1-ethyl-(3-dimethylaminopropyl)carbodiimide (EDC), 1-ethyl-(3-dimethylaminopropyl)carbodiimide hydrochloride (EDC HCl), dicyclohexylcarbodiimide (DCC), carbonylimidazole (CDI), 1-ethoxycarbonyl-2-ethoxy-1,2-dihydroxyquinoline (EEDQ), diphenylphosphorylazide (DPPA) and the like can be used. The condensing agent may be used in an amount of preferably from 0.5 to 20 moles, more preferably from 1 to 10 moles, per mole of the hydrophobic compound. In this case, N-hydroxysuccinimide (HONSu), 1-hydroxybenzotriazole (HOBt), N-hydroxy-5-norbornene-2,3-dicarboxylic acid imide (HONB) or the like may be allowed to coexist.

When a reaction is carried out to link the hydrophobic compound to the raw material copolymer, the amount of the hydrophobic compound to be used is not particularly limited, and it is used generally in an amount of from 0.1 to 2 moles based on one equivalent of carboxyl group of the raw material copolymer.

It is desirable to carry out the condensation reaction in a solvent. For example, N,N-dimethylformamide (DMF), dimethyl sulfoxide (DMSO), dioxane, tetrahydrofuran (THF), water or a mixture solvent thereof may be used as the solvent with no particular limitation. Though not particularly limited, the solvent may be generally used in an amount of from 1 to 500 times by weight more than the raw material copolymer.

The condensation reaction may be carried out at a temperature of preferably from −10 to 50° C., more preferably from −5 to 40° C. The reaction may be sufficient when carried out for 2 to 48 hours.

The high molecular block copolymer-drug complex pharmaceutical preparation of the present invention can be prepared for example by the following methods. In a first method, the thus obtained high molecular block copolymer is dissolved in a solvent. Examples of the solvent to be used can include N,N-dimethylformamide (DMF), dimethyl sulfoxide (DMSO), dioxane, tetrahydrofuran (THF), water, a mixture solvent thereof and the like, of which DMF or a mixture solvent of DMF and water is preferred. The dimer, trimer or tetramer of anthracycline compound is added to this solution in an amount of from 1 to 200% (by weight) based on the high molecular block copolymer, and the mixture is stirred. By replacing the solvent of the mixture solution with water by means of dialysis, ultrafiltration or the like, the high molecular block copolymer-drug complex pharmaceutical preparation of interest is obtained. When other drugs are also to be contained, they may be added together with the dimer, trimer or tetramer of anthracycline compound in an amount of from 1 to 200% by weight based on the high molecular block copolymer.

In a second method, the high molecular block copolymer-drug complex pharmaceutical preparation can also be prepared by carrying out synthesis of the dimer, trimer or tetramer of anthracycline compound simultaneously with introducing it into the high molecular block copolymer. For example, the high molecular block copolymer is dissolved in a solvent. Examples of the solvent to be used can include N,N-dimethylformamide (DMF), dimethyl sulfoxide (DMSO), dioxane, tetrahydrofuran (THF), water, a mixture solvent thereof and the like, of which DMF or a mixture solvent of DMF and water is preferred. The anthracycline compound or a salt thereof (for example, the aforementioned anthracycline anticancer agent) is dissolved in the solution, added with a base and then stirred. By replacing the solvent of the mixture solution with water by means of dialysis, ultrafiltration or the like, the high molecular block copolymer-drug complex pharmaceutical preparation of interest is obtained.

In the second method, the compositional ratio of the dimer, trimer or tetramer of anthracycline compound to the other drugs in the high molecular block copolymer-drug complex pharmaceutical preparation can be controlled in the following manner. For example, the compositional ratio of the dimer, trimer or tetramer of anthracycline compound to the anthracycline compound (the anthracycline anticancer drug) in the high molecular block copolymer-drug complex pharmaceutical preparation to be obtained can be controlled by varying the charge of the anthracycline compound or a salt thereof (an anthracycline anticancer drug) based on the high molecular block copolymer, or by varying the pH value.

The present invention also relates to a high molecular block copolymer-drug complex pharmaceutical preparation in which a high molecular block copolymer having a hydrophilic polymer segment and a hydrophobic polymer segment forms a micelle having the hydrophilic segment as its outer shell, and contains in its hydrophobic inner core an anthracycline anticancer agent, wherein, when the pharmaceutical preparation is intravenously administered to a CDF1 mouse of 7 to 9 week's age, the amount of the anthracycline anticancer agent in 1 ml of the mouse blood plasma after 1 hour of its administration becomes 10 (% of dose/ml) or more, preferably 20 to 60, provided that the amount of anthracycline anticancer agent in the administered preparation is defined as 100.

The aforementioned high molecular block copolymer-drug complex pharmaceutical preparation which contains in the inner core of its micelle the dimer, trimer or tetramer of anthracycline compound together with the anthracycline anticancer agent can be exemplified as such the pharmaceutical preparation.

When a commercially available prior art anticancer agent such as adriamycin is intravenously administered to the human body, its blood level is reduced within an extremely short period of time. On the contrary, when the pharmaceutical preparation of the present invention is intravenously administered, its blood concentration is maintained at a high level for a prolonged period of time, so that anthracycline anticancer agents can be incorporated into tumor tissues in a large quantity, and treatment of cancers therefore can be made effectively.

Since the high molecular block copolymer-drug complex pharmaceutical preparation of the present invention are possessed of high pharmacological effects, when it is used as an anticancer agent for example, its anticancer activity is outstandingly higher than adriamycin whereas their doses are hardly different from each other. In particular, it can show markedly significant action of effecting disappearance of solid cancers. In consequence, it is particularly effective for treating patients of solid cancers such as lung cancer, digestive system cancer, breast cancer, bladder cancer, osteogenic sarcoma and the like. In addition, the high molecular block copolymer-drug complex pharmaceutical preparation of the present invention exerts an excellent effect of being low in toxicity.

The pharmaceutical preparation of the present invention can be used in the conventionally used various dosage forms such as solid formulations, ointments, liquid formulations and the like, which are obtained by mixing it with a pharmaceutically acceptable additive, such as a carrier, filler, diluent, solubilizing agent and the like, and, when used as an anticancer agent, it is generally used in the form of injection which preferably contains 99.99 to 1% of additives based on the total formulation. Its dose is about 10 to 200 mg/m$^2$/week as the total amount of the dimer, trimer or tetramer of anthracycline compound and the other drugs, and it is applied by 1 to 3 divided administration a week.

EXAMPLES

The present invention is described illustratively with reference to the following examples.

Example 1

(1) A 10 mg portion of adriamycin hydrochloride was dissolved in a mixture solvent consisting of 3 ml of DMF, 1 ml of water and 10 μl of triethylamine and allowed to react for 12 hours at 28° C. in the dark. Using a dialysis membrane having a nominal molecular weight cutoff of 1,000, the reaction solution was dialyzed against water to exchange the solvent with water. By separating and purifying this by HPLC, an aqueous solution of a dimer of adriamycin was obtained. This was then freeze-dried to obtain as a solid form the dimer of adriamycin having the structure of formula (AA).

This adriamycin dimer showed the aforementioned infrared absorption spectrum, ultraviolet spectrum and LC/MS mass spectrum. The thus obtained dimer of adriamycin was acid-treated with 1% acetic acid. The mass spectrogram of the resulting product is shown in FIG. 6.

In this connection, the instruments and conditions used for the separation and purification by HPLC and the measurement of the spectra and chromatogram are as described in the foregoing.

(2) A 500 mg portion of adriamycin hydrochloride was dissolved in a mixture solvent consisting of 40 ml of DMF and 40 ml of methanol, and the solution was added with 1.2 ml of triethylamine and allowed to react for 12 hours at 25° C. The reaction solution was purified using a column which has been prepared by packing 350 ml of LH-20 (manufactured by Pharmacia) in a glass tube of 26 mm in inner diameter and 65 cm in length. Methanol was used as the mobile phase in the column purification and was passed through at a flow rate of 5 ml/min. Fractions were collected in 5 ml aliquots, and the fractions of 11th to 25th were pooled, evaporated to dryness and analyzed by a mass spectrometer to confirm the formation of a dimer of adriamycin. As a result of analysis by a high resolution mass spectrometry, its molecular formula was found to be $C_{54}H_{54}N_2O_{21}$.

Figure 8:
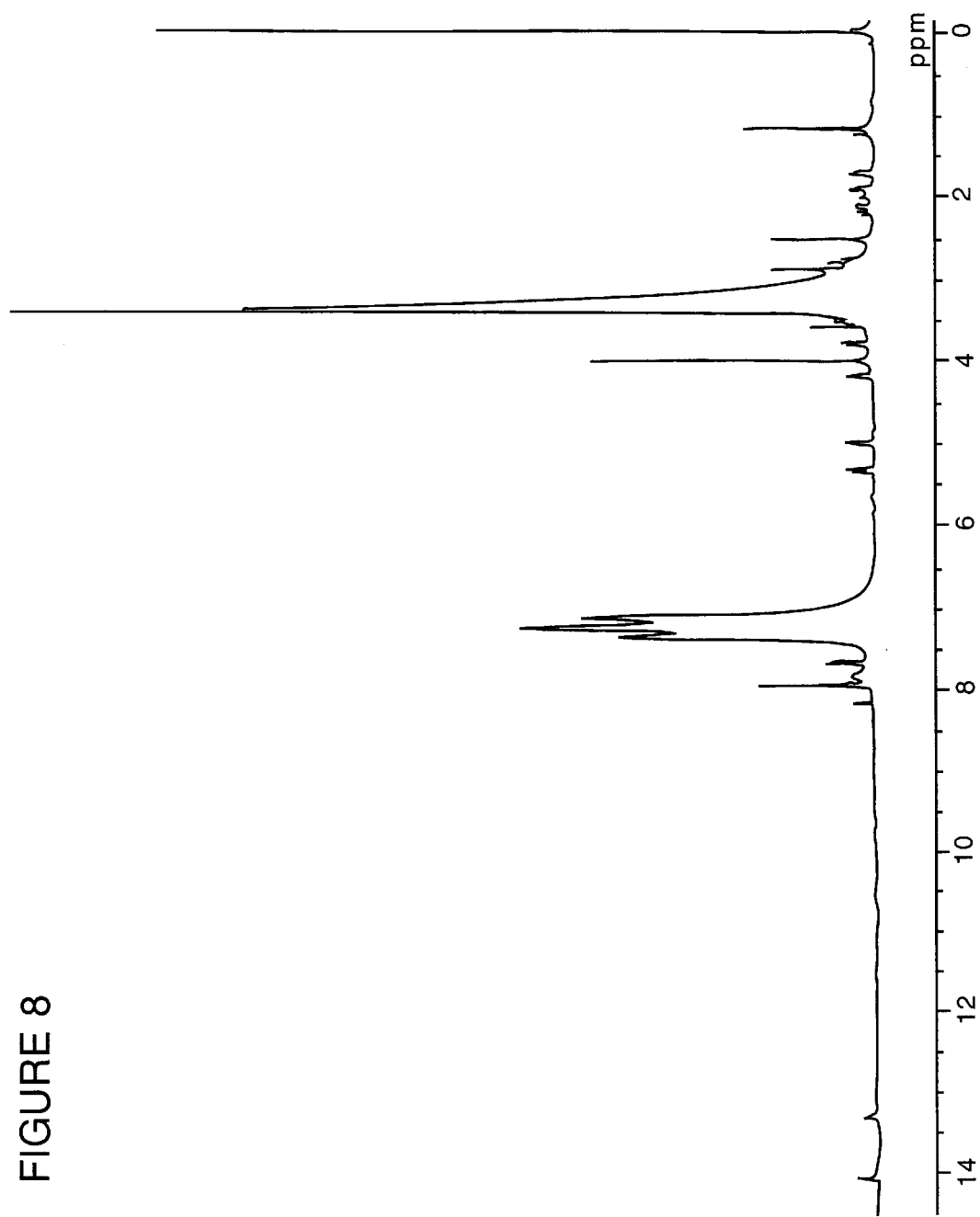
FIGS. 8, 9, 10 or 11 shows a graph of $^1$H one-dimensional spectrum, $^{13}$C one-dimensional spectrum, COSY spectrum or CH COSY spectrum respectively, obtained by the NMR analysis of the separated component from Example 1 (2).
Figure 9:
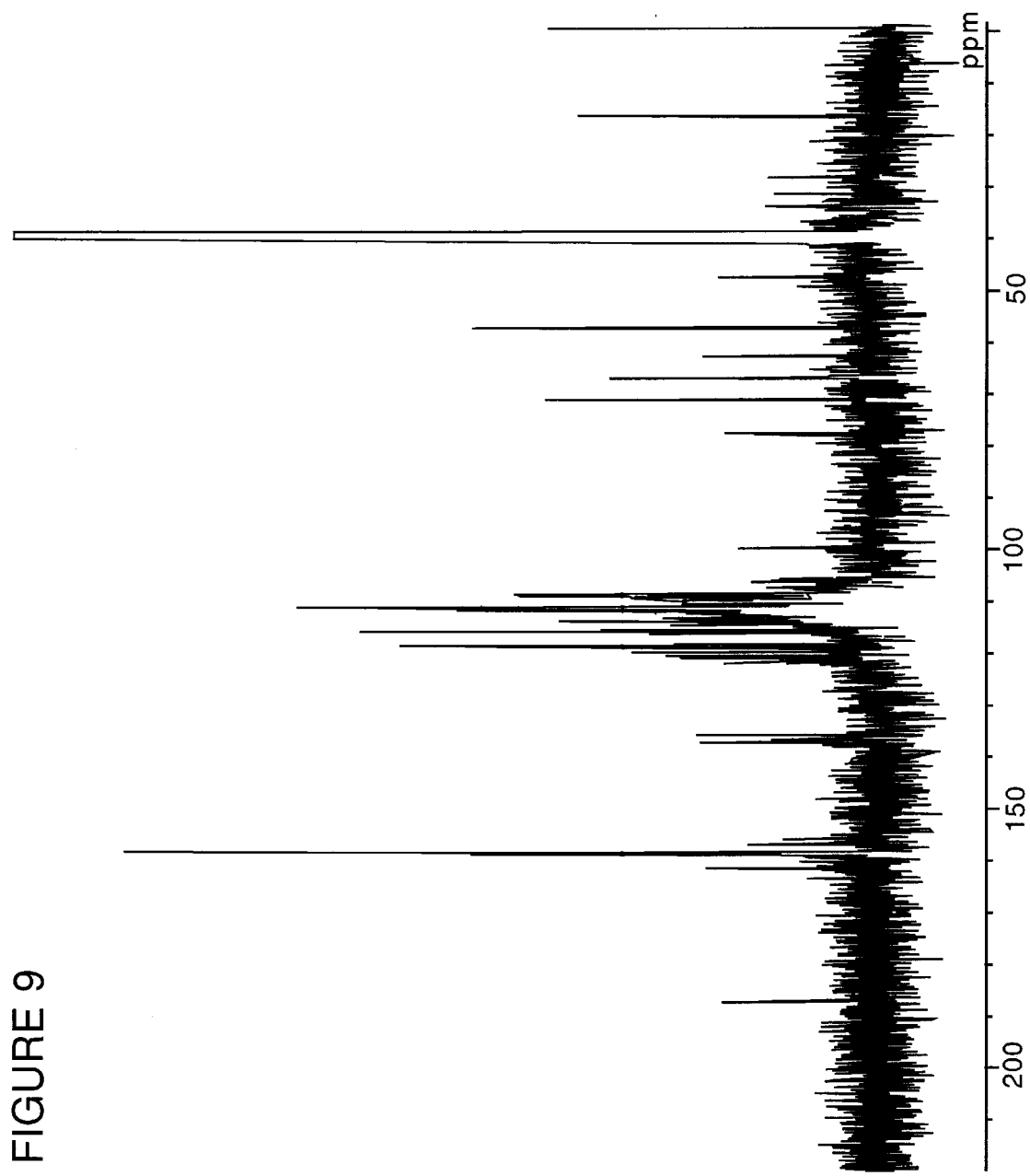
Figure 10:
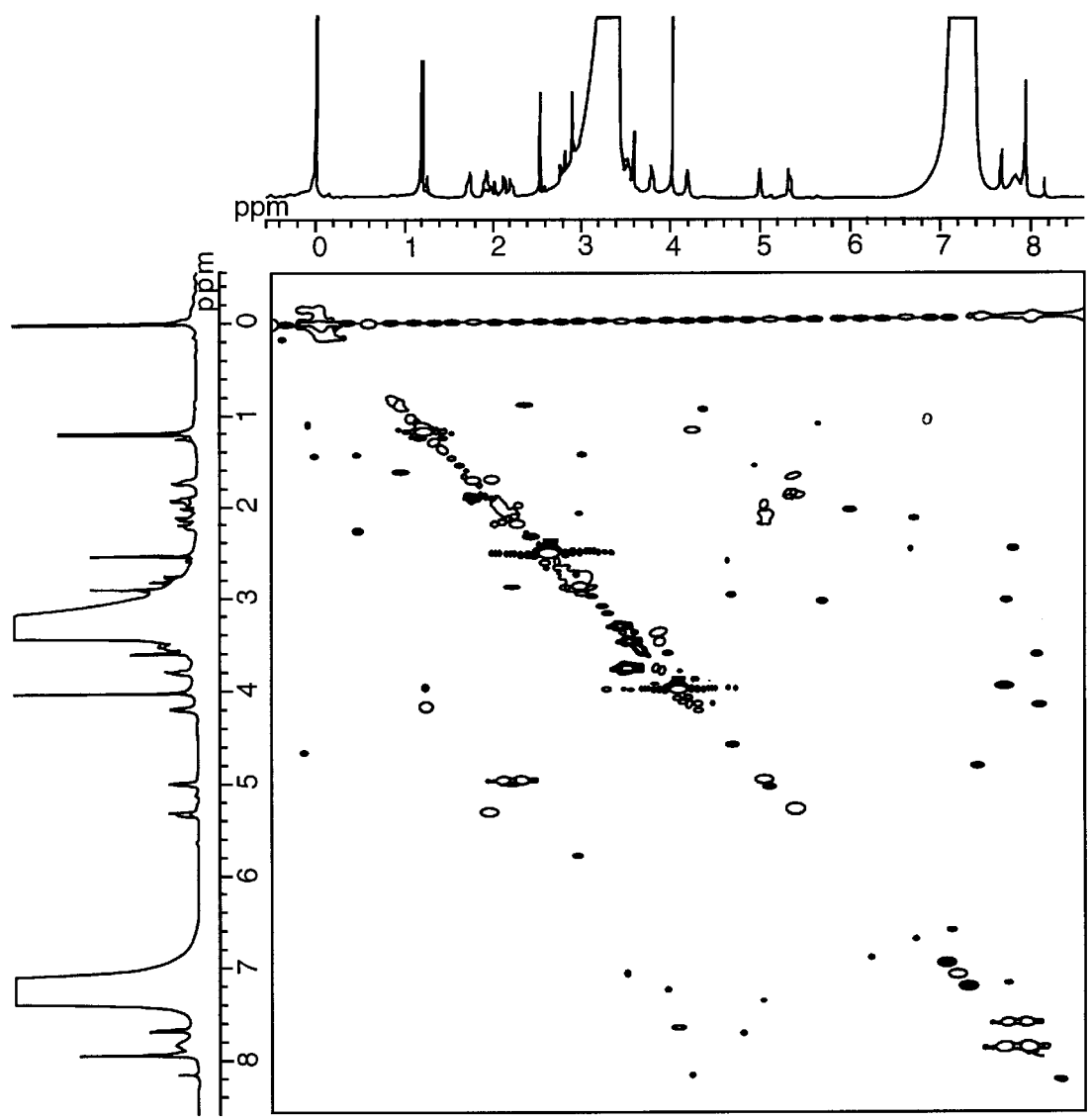
Figure 11:
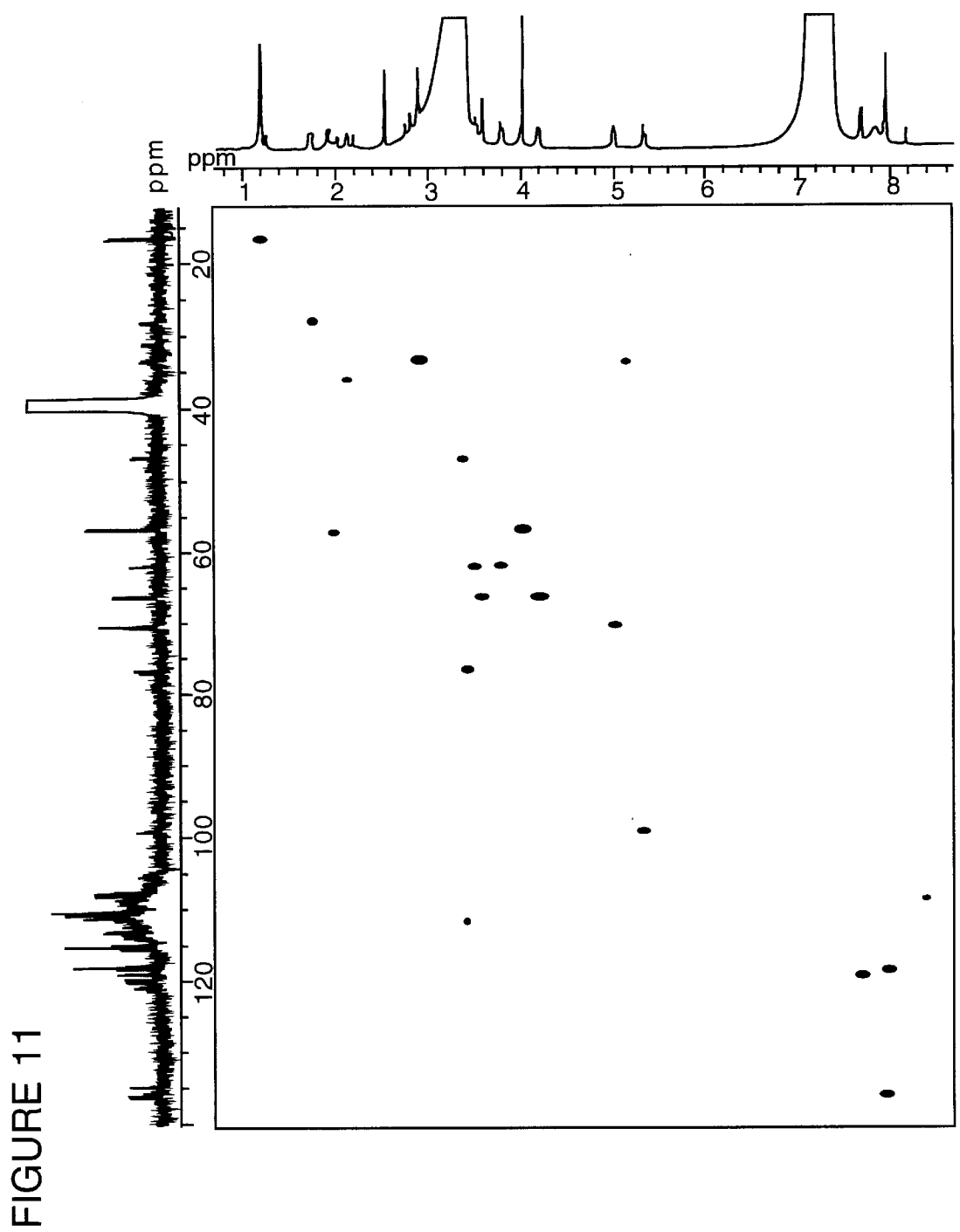

A 10 mg portion of the thus obtained adriamycin dimer was dissolved in 2 ml of methanol, and the solution was added with 1 mg of $NaBH_3CN$, allowed to react for 12 hours at room temperature, mixed with 3 ml of 1 N hydrochloric acid and then reacted for additional 12 hours. The reaction solution was analyzed by LC/MS, and a peak of m/z 524 was separated and analyzed by NMR. The results of NMR analysis resulted in the $^1H$ one-dimensional spectrum shown in FIG. 8, the $^{13}C$ one-dimensional spectrum shown in FIG. 9, the COSY spectrum shown in FIG. 10 and the CH COSY spectrum shown in FIG. 11.

On the basis of these results, it was confirmed to be the dimer of adriamycin having the structure of formula (AA).

(3) A 500 mg portion of adriamycin hydrochloride was dissolved in a mixture solvent consisting of 40 ml of DMF and 40 ml of methanol, and the solution was added with 1.2 ml of triethylamine and allowed to react for 12 hours at 25° C. The reaction solution was purified using a column which has been prepared by packing 350 ml of LH-20 (manufactured by Pharmacia) in a glass tube of 26 mm in inner diameter and 65 cm in length. Methanol was used as the mobile phase in the column purification and was passed through at a flow rate of 5 ml/min. Fractions were collected in 5 ml aliquots, and the fractions of 5th to 9th were pooled, evaporated to dryness and analyzed by a mass spectrometer to obtain the mass spectrum shown in FIG. 7. The result confirmed the formation of a trimer of adriamycin.

Example 2

A 5 mg portion of adriamycin hydrochloride and 5 mg of daunomycin hydrochloride were dissolved in a mixture solvent consisting of 3 ml of DMF, 1 ml of water and 10 µl of triethylamine and allowed to react for 12 hours at 28° C. in the dark. Without purification, the reaction solution was subjected to a mass spectrum analysis by LC/MS to confirm the formation of a dimer of adriamycin and the formation of a dimer of daunomycin with adriamycin.

Figure 12:
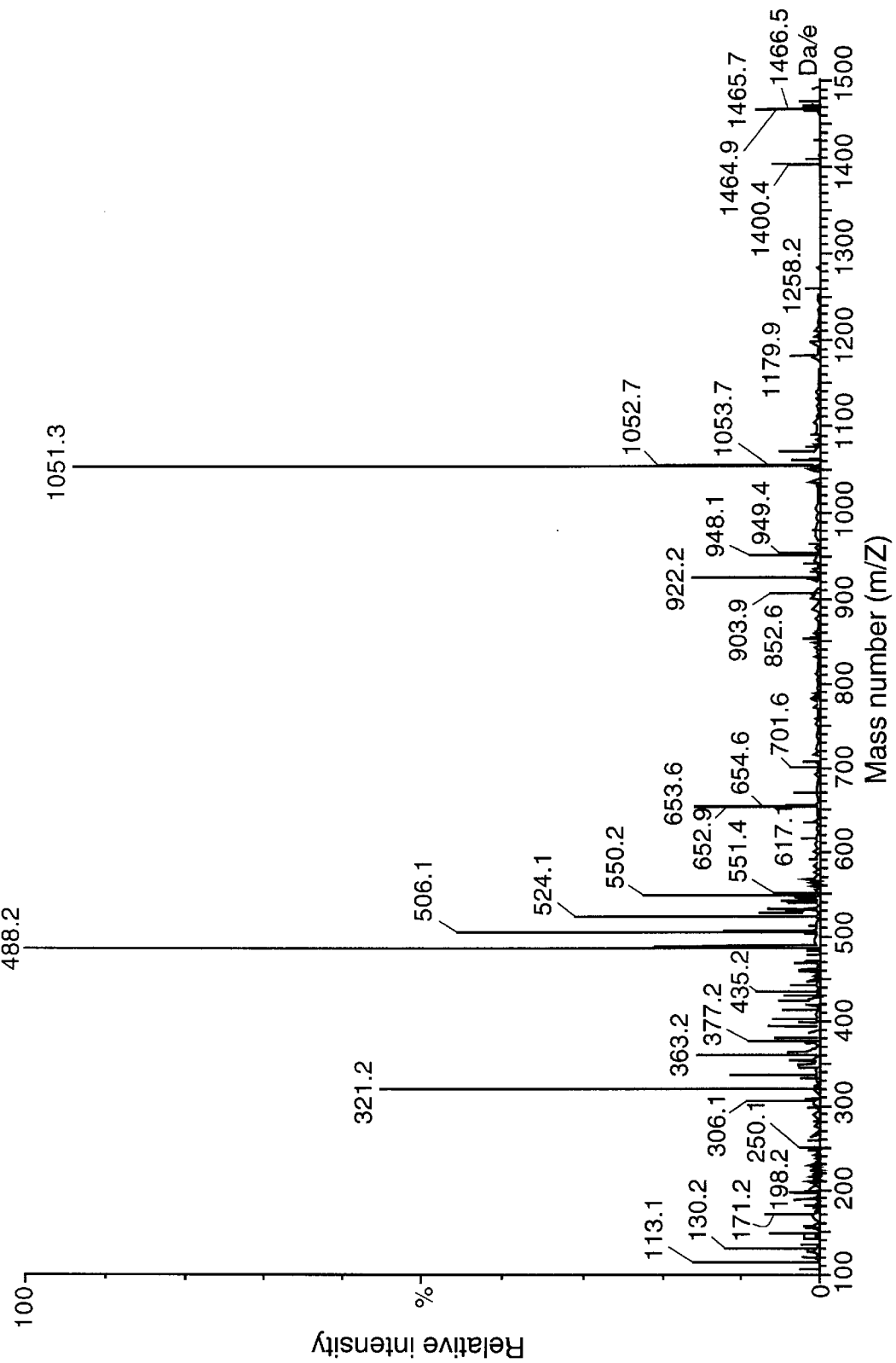
FIG. 12 shows a graph of mass spectrum of the dimer of daunomycin with adriamycin.

Of these products, the adriamycin dimer showed the same mass spectrum described in the foregoing. The mass spectrum of the dimer of daunomycin with adriamycin is shown in FIG. 12. Under these reaction conditions, a daunomycin dimer was not formed. In this connection, the instruments and conditions for obtaining these spectra are as described in the foregoing.

Mass spectrum of the dimer of daunomycin with adriamycin (ESI), m/z (%): 1051 (90), 948 (15), 922 (20), 904 (10), 653 (20), 524 (30), 506 (50), 488 (100).

Example 3

Figure 13:
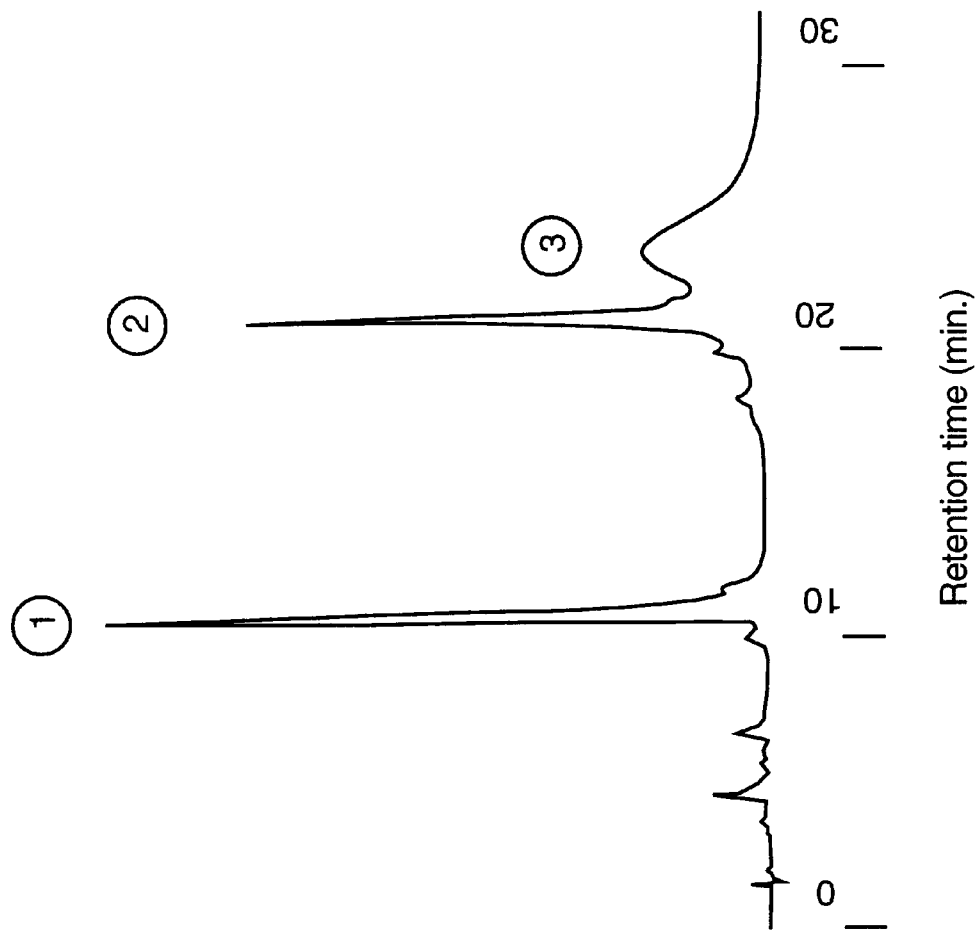
FIG. 13 shows a graph of HPLC chromatogram of the pharmaceutical preparation obtained from Example 3.

A 20.0 g portion of polyethylene glycol having a methoxy group on one terminal and an 3-aminopropyl group on the other terminal ($PEG-NH_2$) (molecular weight 13,900) was dissolved in 100 ml of N,N-dimethylformamide (DMF). To this solution was added 15.0 g of p-benzyl-L-aspartate-N-carboxylic anhydride (BLA-NCA). With stirring in a water bath of 35° C., the polymerization reaction was carried out for 24 hours. Next, while stirring in an ice bath, the polymerization solution was added to an aqueous 0.5 N sodium hydroxide solution and stirred for 20 minutes. Next, this was adjusted to a pH value of approximately 4 by adding 2 N hydrochloric acid, diluted with distilled water to a total volume of 20 liters and then adjusted to pH 4. Next, a procedure of concentrating and washing it was repeated using a hollow fiber type ultrafiltration apparatus (Amicon CH2, molecular weight cutoff after ultrafiltration=10,000). Next, the thus concentrated solution was purified using a sulfonic acid type ion exchange resin (Amberlite IR-120B) column. The resulting eluate was concentrated under a reduced pressure and then freeze-dried to obtain 19.58 g of a polyethylene glycol-polyaspartic acid block copolymer (PEG-P(Asp.)). A 5.008 g portion of the PEG-P(Asp.) was dissolved in 83 ml of DMF to which was subsequently added 83 ml of acetonitrile. This was added with 8.979 g of dicyclohexylcarbodiimide (DCC), stirred for 5 minutes and then added with a solution which has been prepared by dissolving 2.528 g of adriamycin hydrochloride in 167 ml of DMF and adding 786 µl of triethylamine thereto. Next, this was allowed to react for 4 hours while stirring at room temperature. After the reaction, this was added with 16.7 ml of an aqueous 1% phosphoric acid solution and stirred for 5 minutes. After its dialysis using a dialysis membrane (molecular weight cutoff=12,000~14,000), the precipitate originated from DCC was removed by filtration. The resulting filtrate was purified using a hollow fiber type ultrafiltration apparatus (Amicon CH2, molecular weight cutoff of ultrafiltration membrane=10,000). This was further concentrated by ultrafiltration using an ultrafiltration membrane of ADVANTEC UK-50 (molecular weight cutoff=50,000) to obtain 177 ml of an aqueous solution having a concentration of 12 mg/ml as adriamycin (calculated from its absorbance at 485 nm measured by an ultraviolet ray spectrophotometer). The thus obtained PEG-P(Asp.)ADR has the structure of the aforementioned formula (2) in which $R_1$ is a methyl group, $R_2$ is a trimethylene group, $R_3$ is a methylene group, a portion of $R_4$ is a hydroxyl group and the rest thereof is the aforementioned residue of formula (3) [Y is $CH_2OH$, Z is H], $R_5$ is hydrogen, n=315, m=30 and x=8. The adriamycin content was 32.3% by weight, and it showed appropriate water solubility. A 20 ml portion of the aqueous solution containing 12 mg/ml (as adriamycin) of the thus obtained PEG-P(Asp.)ADR was mixed with a solution which has been prepared by dissolving 258.8 mg of adriamycin hydrochloride in 60 ml of DMF and adding 100 µl of triethylamine thereto, and the mixture was stirred at room temperature for 2 hours in the dark. After dialysis using a dialysis membrane (molecular weight cutoff=12,000~14,000), the resulting solution was freeze-dried. This was purified and concentrated by redissolving it in water and carrying out ultrafiltration using an ultrafiltration membrane of ADVANTEC UK-50 (molecular weight cutoff=50,000). This was further filtered using a 0.45 µm filter to obtain 25.3 ml of an aqueous solution of a block copolymer-drug complex pharmaceutical preparation. The thus obtained aqueous solution was found to have the HPLC chromatogram shown in FIG. 13. In the drawing, the peak ① is adriamycin, the peak ② is the dimer of adriamycin and the broad peak ③ is adriamycin linked to the polymer. The concentration of adriamycin (peak ①) was 3.06 mg/ml, and the concentration of the adriamycin dimer (peak ②) was 3.18 mg/ml. The weight ratio of adriamycin to the adriamycin dimer was 1:1.04.

The measuring conditions of HPLC are as follows.

Column: C4·300 angstrom/5 µm, manufactured by Waters

Eluent: acetonitrile/1% acetic acid+40 mM sodium dodecyl sulfate

| Gradient elution | | | | | | |
|---|---|---|---|---|---|---|
| Time (minute) | 0 | 4 | 12 | 25 | 30 | 31 |
| Acetonitrile concentration (%) | 15 | 35 | 35 | 85 | 85 | 15 |

Detection: 485 nm

Flow rate: 1 ml/min

Example 4

Figure 14:
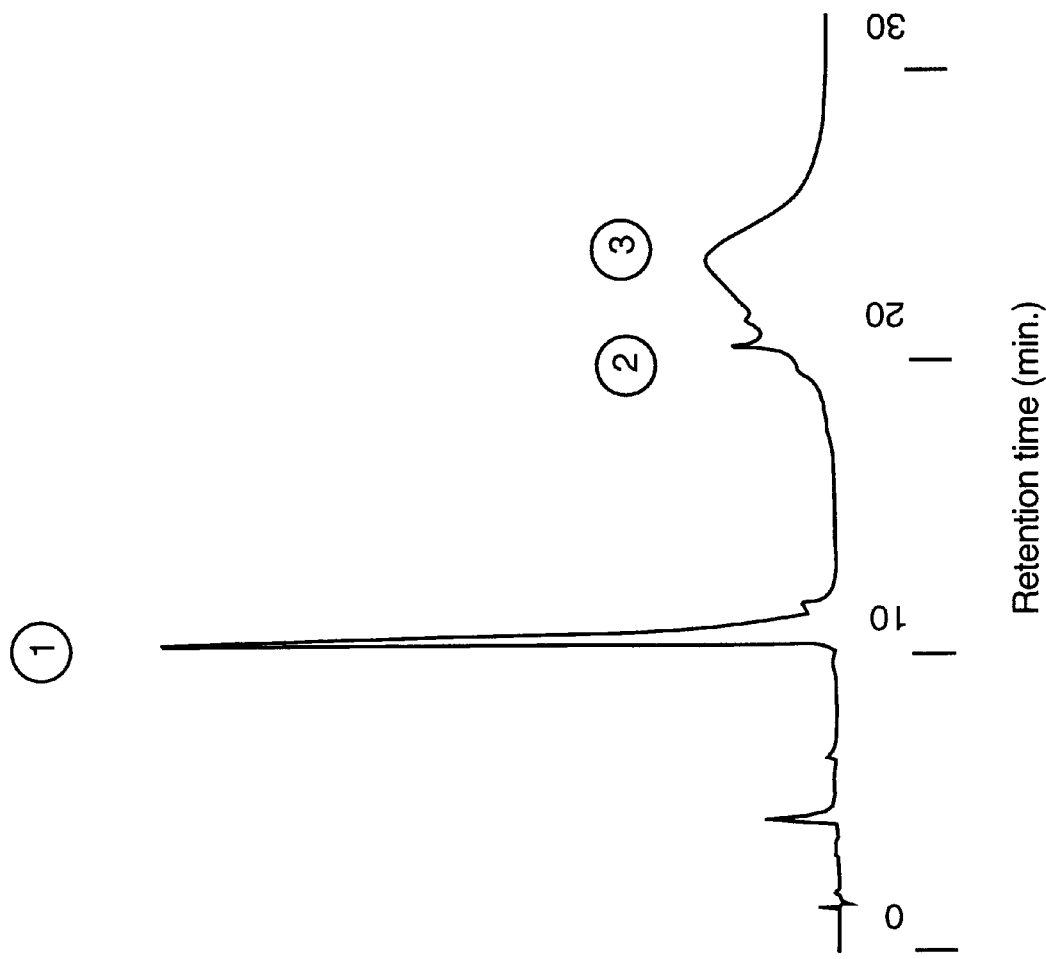
FIG. 14 shows a graph of HPLC chromatogram of the pharmaceutical preparation obtained from Example 4.

A 20 ml portion of the aqueous solution containing 12 mg/ml (as adriamycin) of PEG-P(Asp.)ADR prepared in Example 3 was mixed with a solution which has been prepared by dissolving 102.4 mg of adriamycin hydrochloride in 60 ml of DMF and adding 32 μl of triethylamine thereto, and the mixture was stirred at room temperature for 2 hours in the dark. After dialysis using a dialysis membrane (molecular weight cutoff=12,000~14,000), the resulting solution was freeze-dried. This was purified and concentrated by redissolving it in water and carrying out ultrafiltration using an ultrafiltration membrane of ADVANTEC UK-50 (molecular weight cutoff=50,000). This was further filtered using a 0.45 μm filter to obtain 20.4 ml of an aqueous solution of a block copolymer-drug complex pharmaceutical preparation. The thus obtained aqueous solution was found to have the HPLC chromatogram shown in FIG. 14. In the drawing, the peak ① is adriamycin, the peak ② is the dimer of adriamycin and the broad peak ③ is adriamycin linked to the polymer. The concentration of adriamycin (peak ①) was 3.01 mg/ml, and the concentration of the adriamycin dimer (peak ②) was 0.39 mg/ml. The weight ratio of adriamycin to the adriamycin dimer was 1:0.13. The HPLC measuring conditions are as described in Example 3.

Example 5

Figure 15:
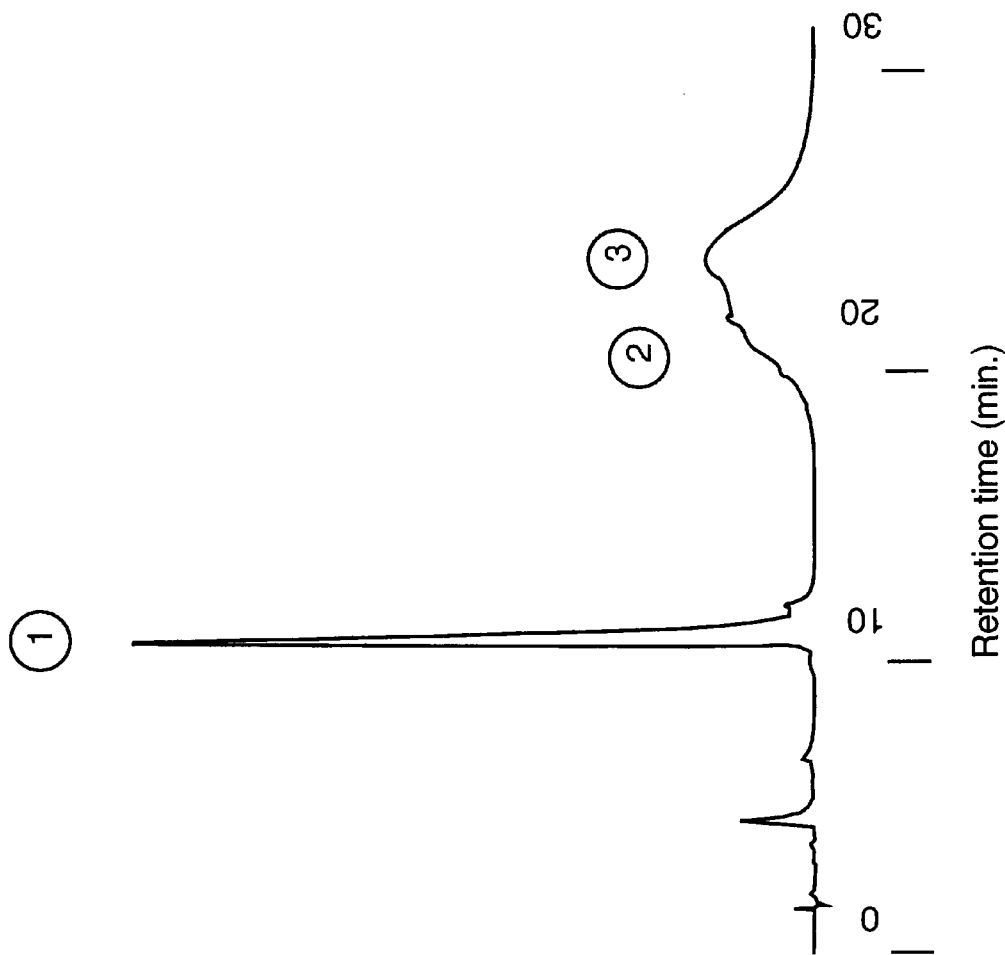
FIG. 15 shows a graph of HPLC chromatogram of the pharmaceutical preparation obtained from Example 5.

A 20 ml portion of the aqueous solution containing 12 mg/ml (as adriamycin) of PEG-P(Asp.)ADR prepared in Example 3 was diluted with 20 ml of water and then freeze-dried. This was redissolved in 20 ml of water, and pH value of the solution was adjusted with acetic acid and an aqueous sodium acetate solution in such amounts that the solution finally became 40 ml of 30 mM acetate buffer (pH 5.0) solution. The thus prepared solution was mixed with 128.0 mg of adriamycin hydrochloride and stirred at room temperature for 2 days in the dark. After dialysis using a dialysis membrane (molecular weight cutoff=12,000~14,000), this was purified and concentrated by carrying out ultrafiltration using an ultrafiltration membrane of ADVANTEC UK-50 (molecular weight cutoff=50,000) to obtain 16.7 ml of an aqueous solution of a block copolymer-drug complex pharmaceutical preparation. The thus obtained aqueous solution was found to have the HPLC chromatogram shown in FIG. 15. In the drawing, the peak ① is adriamycin, the peak ② is the dimer of adriamycin and the broad peak ③ is adriamycin linked to the polymer. The concentration of adriamycin (peak ①) was 2.99 mg/ml, and the concentration of the adriamycin dimer (peak ②) was 0.27 mg/ml. The weight ratio of adriamycin to the adriamycin dimer was 1:0.09. The HPLC measuring conditions are as described in Example 3.

Application Example 1

Figure 16:
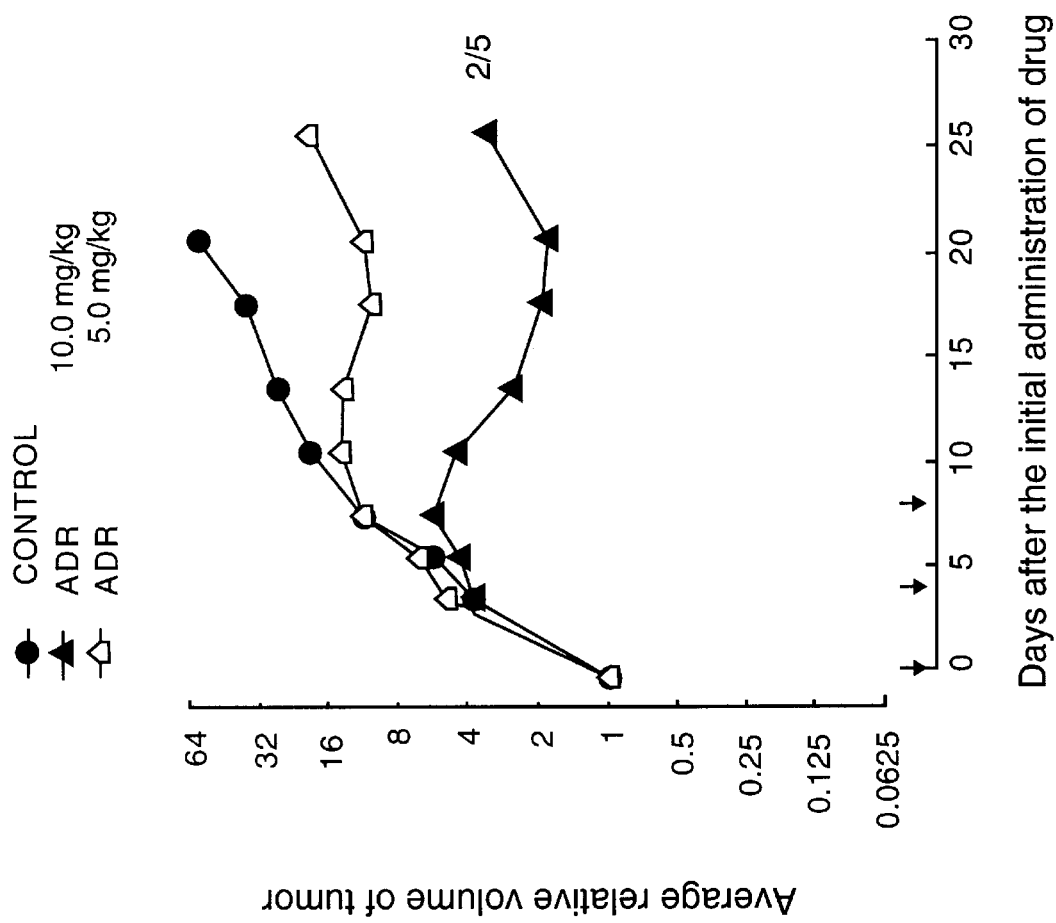
FIG. 16 shows a graph of tumor growth curve of mouse Colon 26 adenocarcinoma when the mouse was administered with adriamycin hydrochloride in Application Example 1.
Figure 17:
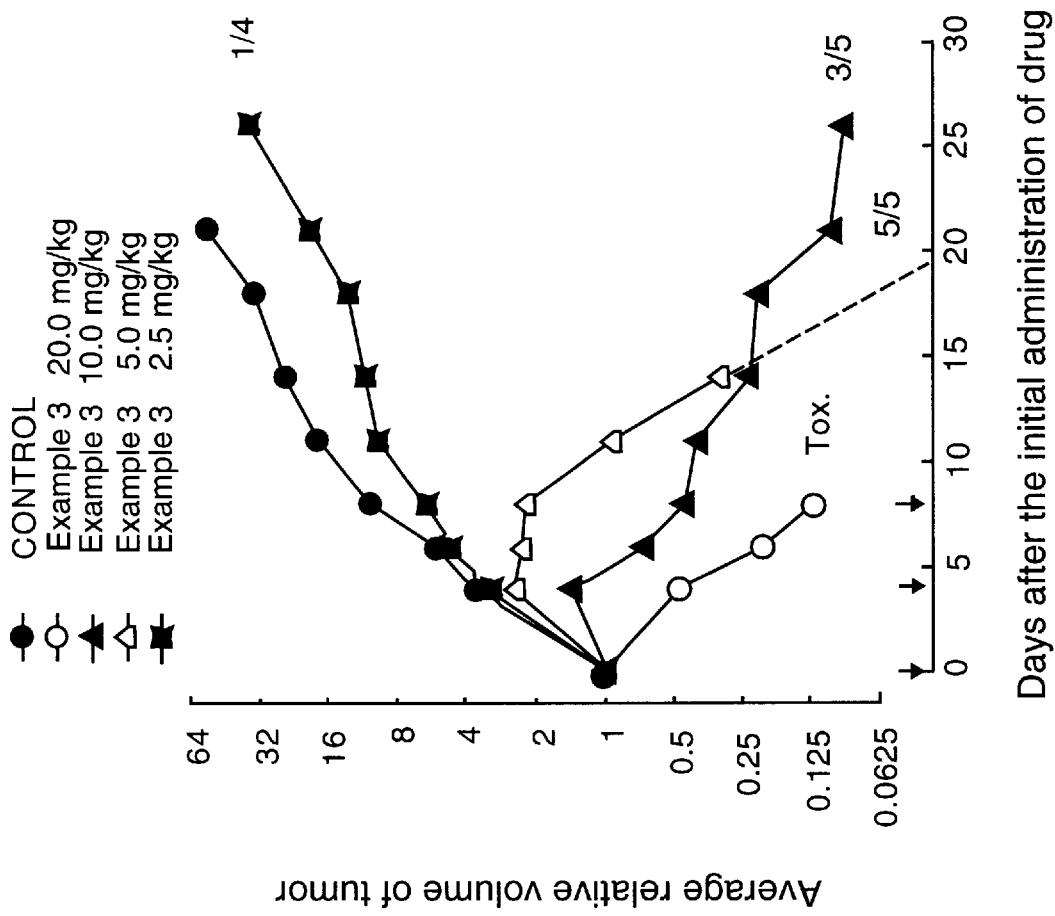
FIG. 17 shows a graph of tumor growth curve of mouse Colon 26 adenocarcinoma when the mouse was administered with the pharmaceutical preparation of Example 3 in Application Example 1.

Colon 26 adenocarcinoma cells were transplanted subcutaneously in the subaxillary region of each CDF1 female mouse. When the volume of the tumor reached around 100 mm$^3$, the block copolymer-drug complex pharmaceutical preparation synthesized in Example 3, 4 or 5 or adriamycin hydrochloride was intravenously administered once a day every 4th day in total of three times (indicated by arrows in the drawings) to examine their antitumor effects. Each drug was used by diluting it in physiological saline prior to its use. Each dose was determined as the amount of adriamycin of the peak ① of the HPLC chromatogram. The antitumor effects of each drug were estimated based on the tumor growth curve, the number of mice in which the tumor disappeared and the chemotherapeutic index. The results are shown in Tables 1 and 2 and FIGS. 16 and 17. In comparison with the case of the administration of adriamycin hydrochloride, larger number of tumor-disappeared mice was observed with broader range of dose when the block copolymer-drug complex pharmaceutical preparations of Examples 3 to 5 were administered. Particularly, the pharmaceutical preparation of Example 3 having a higher adriamycin dimer content showed the most excellent results in the complete cure ratio and the chemotherapeutic index.

TABLE 1

Antitumor activity on mouse Colon 26 adenocarcinoma

| Sample | Dose (mg/kg) | Tumor-disappeared mice |
|---|---|---|
| Adriamycin hydrochloride | 5 | 0/5 |
|  | 10 | 2/5 |
| Pharmaceutical preparation of Example 3 | 2.5 | 1/4 |
|  | 5 | 5/5 |
|  | 10 | 3/5 |
| Pharmaceutical preparation of Example 4 | 2.5 | 0/5 |
|  | 5 | 1/5 |
|  | 10 | 4/5 |
| Pharmaceutical preparation of Example 5 | 2.5 | 0/5 |
|  | 5 | 2/5 |
|  | 10 | 3/5 |

TABLE 2

Comparison of chemotherapeutic index

| Sample | LD$_{50}$ | Min T/C$_{42}$ [1] | C. index [2] |
|---|---|---|---|
| Adriamycin hydrochloride | 15 | 5.95 | 2.52 |
| Pharmaceutical preparation of Example 3 | 15 | 2.59 | 5.78 |
| Pharmaceutical preparation of Example 4 | 15 | 4.88 | 3.08 |
| Pharmaceutical preparation of Example 5 | 15 | 6.02 | 2.49 |

[1] Minimum dose when T/C (%) becomes 42% or less on the 14th day after the initial administration
[2] Chemotherapeutic index: LD$_{50}$/(Min T/C$_{42}$)

Example 6

Figure 18:
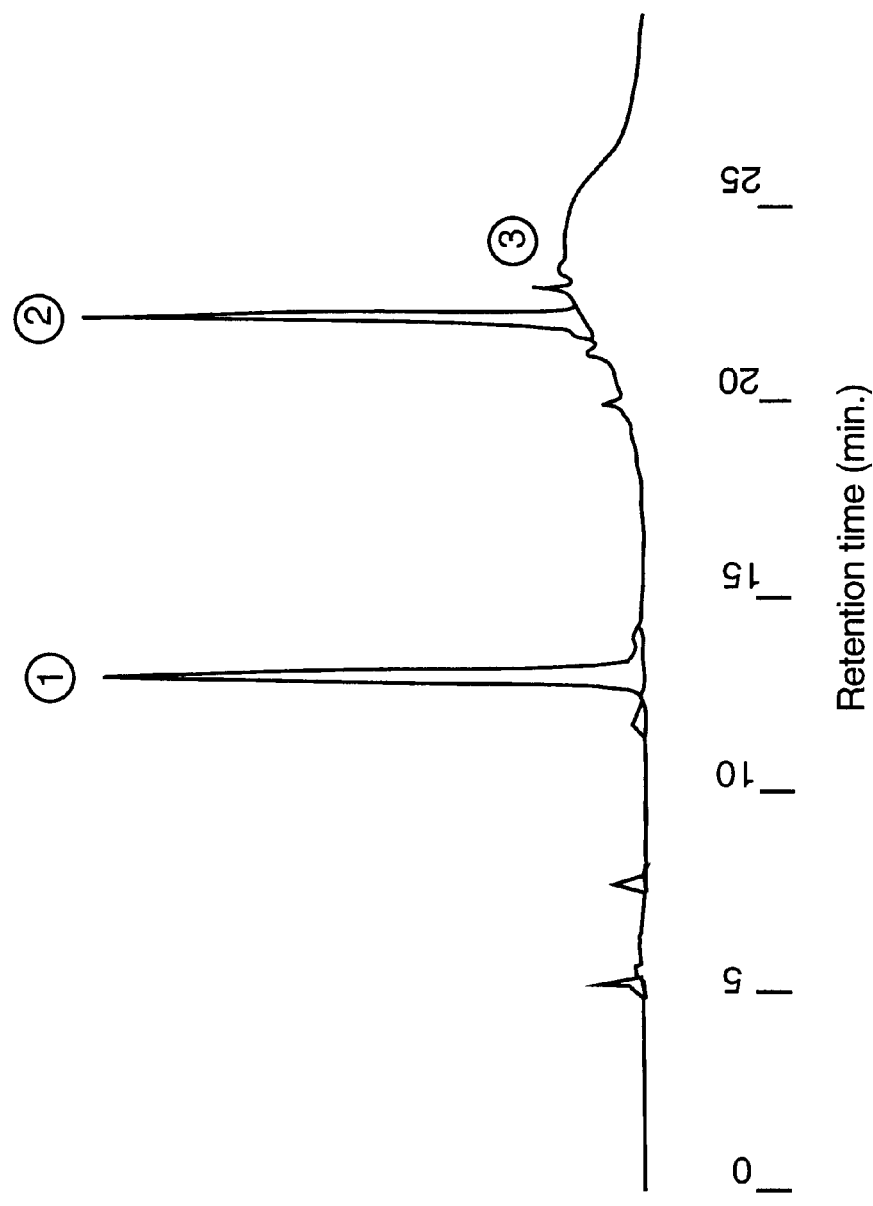
FIG. 18 shows a graph of HPLC chromatogram of the pharmaceutical preparation obtained from Example 6.

A 20.0 g portion of polyethylene glycol having a methoxy group on one terminal and an 3-aminopropyl group on the other terminal (PEG-NH$_2$) (molecular weight 14,200) was dissolved in 100 ml of N,N-dimethylformamide (DMF). To this solution was added 15.0 g of β-benzyl-L-aspartate-N-carboxylic anhydride (BLA-NCA), followed by the polymerization reaction being carried out for 24 hours with stirring in a water bath of 35° C. Next, while stirring in an ice bath, the polymerization solution was added to an aqueous 0.5 N sodium hydroxide solution and stirred for 20 minutes. This was adjusted to a pH value of approximately 4 by adding 2 N hydrochloric acid, diluted with distilled water to a total volume of 20 liters and then adjusted to pH 4. A procedure of concentrating and washing it was repeated using a hollow fiber type ultrafiltration apparatus (Amicon CH2, molecular weight cutoff of ultrafiltration membrane= 10,000). Next, the thus concentrated solution was purified using a sulfonic acid type ion exchange resin (Amberlite IR-120B) column. The resulting eluate was concentrated under a reduced pressure and then freeze-dried to obtain 21.26 g of a polyethylene glycol-polyaspartic acid block copolymer (PEG-P(Asp.)). A 7.501 g portion of the PEG-P (Asp.) was dissolved in 125 ml of DMF to which was subsequently added 125 ml of acetonitrile. Next, this was added with 12.992 g of dicyclohexylcarbodiimide (DCC), stirred for 5 minutes and then added with a solution which has been prepared by dissolving 3.654 g of adriamycin hydrochloride in 250 ml of DMF and adding 1.14 ml of triethylamine thereto. Next, this was allowed to react for 4 hours while stirring at room temperature. After the reaction, this was added with 25 ml of an aqueous 1% phosphoric acid solution and stirred for 5 minutes. After its dialysis using a dialysis membrane (molecular weight cutoff=12,000~14, 000), the precipitate originated from DCC was removed by filtration. The resulting filtrate was purified using a hollow fiber type ultrafiltration apparatus (Amicon CH2, molecular weight cutoff of ultrafiltration membrane=10,000) and then concentrated by ultrafiltration using an ultrafiltration membrane of ADVANTEC UK-50 (molecular weight cutoff=50, 000) to obtain 270 ml of an aqueous solution having a concentration of 12 mg/ml as adriamycin (calculated from its absorbance at 485 nm measured by an ultraviolet ray spectrophotometer). The thus obtained PEG-P(Asp.)ADR has the structure of the aforementioned formula (2) in which $R_1$ is a methyl group, $R_2$ is a trimethylene group, $R_3$ is a methylene group, a portion of $R_4$ is a hydroxyl group and the rest thereof is the aforementioned residue of formula (3) [Y is $CH_2OH$, Z is H], $R_5$ is hydrogen, n=325, m=30 and x=8. The adriamycin content was 32.4%, and it showed appropriate water solubility. A 1 ml portion of the aqueous solution containing 12 mg/ml (as adriamycin) of the thus obtained PEG-P(Asp.)ADR was mixed with a solution which has been prepared by dissolving 11.93 mg of $^{14}$C-labeled adriamycin hydrochloride in 3 ml of DMF and adding 4.9 μl of triethylamine thereto, and the mixture was stirred at room temperature for 2 hours in the dark. After dialysis using a dialysis membrane (molecular weight cutoff=12,000~14,000), the resulting solution was purified and concentrated by carrying out ultrafiltration using an ultrafiltration membrane of ADVANTEC UK-50 (molecular weight cutoff=50,000) to obtain 3.0 ml of an aqueous solution of a block copolymer-drug complex pharmaceutical preparation. The thus obtained aqueous solution was found to have the HPLC chromatogram shown in FIG. 18. In the drawing, the peak ① is adriamycin, the peak ② is the dimer of adriamycin and the broad peak ③ is adriamycin linked to the polymer. The concentration of adriamycin (peak ①) was 1.29 mg/ml, and the concentration of the adriamycin dimer (peak ②) was 1.36 mg/ml. The weight ratio of adriamycin to the adriamycin dimer was 1:1.05. The measuring conditions of HPLC are as described in Example 3.

Example 7

Figure 19:
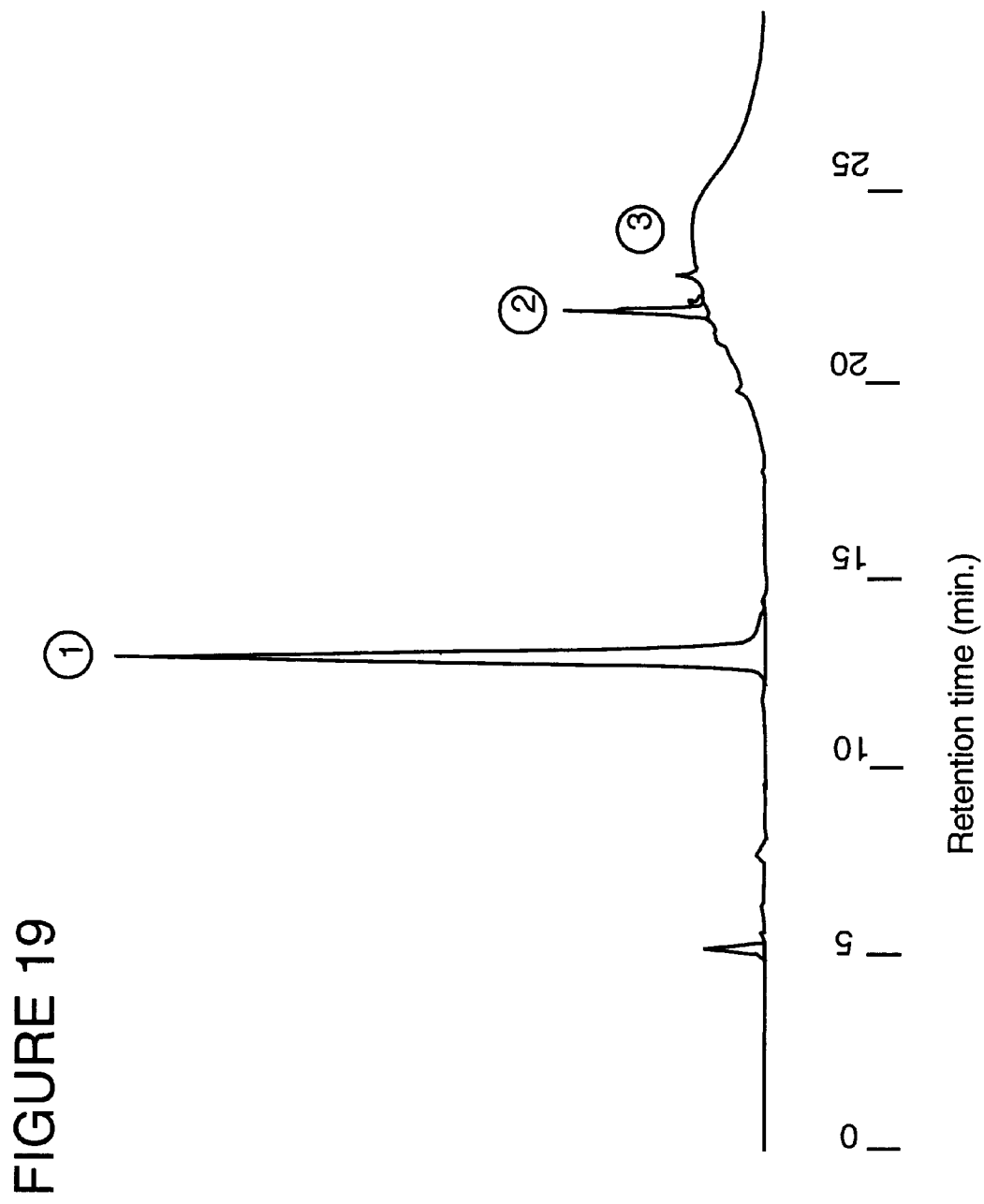
FIG. 19 shows a graph of HPLC chromatogram of the pharmaceutical preparation obtained from Example 7.

A 2.08 ml portion of the aqueous solution containing 12 mg/ml (as adriamycin) of the PEG-P(Asp. )ADR prepared in Example 6 was mixed with a solution which has been prepared by dissolving 9.86 mg of $^{14}$C-labeled adriamycin hydrochloride in 6.25 ml of DMF and adding 3.3 μl of triethylamine thereto, and the mixture was stirred at room temperature for 2 hours in the dark. After dialysis using a dialysis membrane (molecular weight cutoff=12,000~14, 000), the resulting solution was purified and concentrated by carrying out ultrafiltration using an ultrafiltration membrane of ADVANTEC UK-50 (molecular weight cutoff=50,000) to obtain 2.3 ml of an aqueous solution of a block copolymer-drug complex pharmaceutical preparation. The thus obtained aqueous solution was found to have the HPLC chromatogram shown in FIG. 19. In the drawing, the peak ① is adriamycin, the peak ② is the dimer of adriamycin and the broad peak ③ is adriamycin linked to the polymer. The concentration of adriamycin (peak ①) was 3.41 mg/ml, and the concentration of the adriamycin dimer (peak ②) was 0.95 mg/ml. The weight ratio of adriamycin to the adriamycin dimer was 1:0.28. The measuring conditions of HPLC are as described in Example 3.

Example 8

Figure 20:
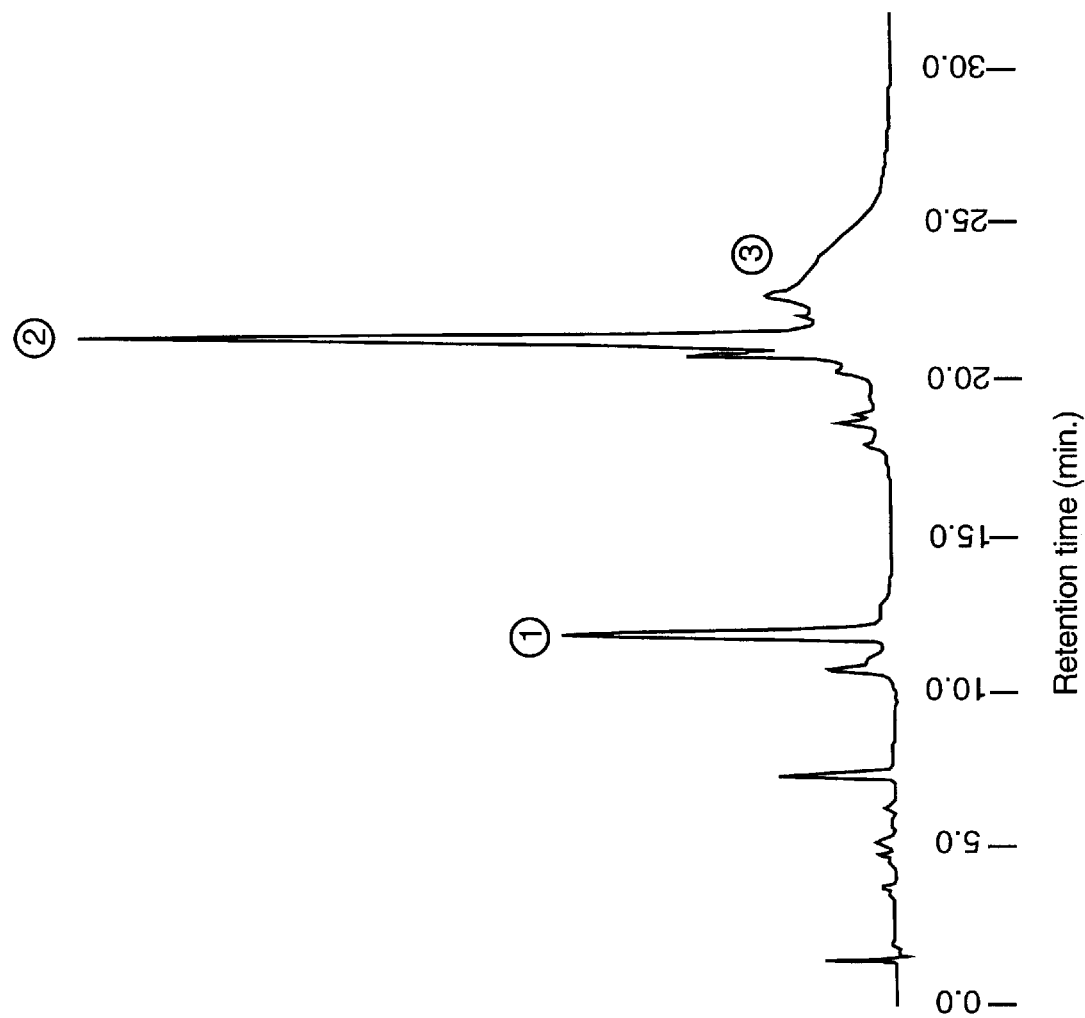
FIG. 20 shows a graph of HPLC chromatogram of the pharmaceutical preparation obtained from Example 8.

A 20.0 g portion of polyethylene glycol having a methoxy group on one terminal and an 3-aminopropyl group on the other terminal (PEG-$NH_2$) (molecular weight 14,500) was dissolved in 100 ml of N,N-dimethylformamide (DMF). To this solution was added 15.0 g of P-benzyl-L-aspartate-N-carboxylic anhydride (BLA-NCA), followed by the polymerization reaction being carried out for 24 hours with stirring in a water bath of 35° C. Next, while stirring in an ice bath, the polymerization solution was added to an aqueous 0.5 N sodium hydroxide solution and stirred for 20 minutes. This was adjusted to a pH value of approximately 4 by adding 2 N hydrochloric acid, diluted with distilled water to a total volume of 20 liters and then adjusted to pH 4. A procedure of concentrating and washing it with water was repeated using a hollow fiber type ultrafiltration apparatus (Amicon CH2, molecular weight cutoff of ultrafiltration membrane=10,000). Next, the thus concentrated solution was purified using a sulfonic acid type ion exchange resin (Amberlite IR-120B) column. The resulting eluate was concentrated under a reduced pressure and then freeze-dried to obtain 19.01 g of a polyethylene glycol-polyaspartic acid block copolymer (PEG-P(Asp.)). A 5.010 g portion of the PEG-P(Asp.) was dissolved in 83 ml of DMF to which was subsequently added 83 ml of acetonitrile. Next, this was mixed with 8.693 g of dicyclohexylcarbodiimide (DCC), stirred for 5 minutes and then added with a solution which has been prepared by dissolving 2.445 g of adriamycin hydrochloride in 167 ml of DMF and adding 759 μl of triethylamine thereto. Next, this was allowed to react for 4 hours while stirring at room temperature. After the reaction, this was added with 16.7 ml of an aqueous 0.5% phosphoric acid solution and stirred for 5 minutes. After its dialysis using a dialysis membrane (molecular weight cutoff=12, 000~14,000), the precipitate originated from DCC was removed by filtration. The resulting filtrate was concentrated by carrying out ultrafiltration using an ultrafiltration membrane of ADVANTEC UK-50 (molecular weight cutoff=50, 000) to obtain 185 ml of an aqueous solution having a concentration of 12 mg/ml as adriamycin (calculated from its absorbance at 485 nm measured by an ultraviolet ray spectrophotometer). The thus obtained PEG-P(Asp.)ADR has the structure of the aforementioned formula (2) in which $R_1$ is a methyl group, $R_2$ is a trimethylene group, $R_3$ is a methylene group, a portion of $R_4$ is a hydroxyl group and the rest thereof is the aforementioned residue of formula (3) [Y is $CH_2OH$, Z is H], $R_5$ is hydrogen, n=350, m=32 and x=8. The adriamycin content was 30.2%, and it showed appropriate water solubility. A 20 ml portion of the aqueous solution containing 12 mg/ml (as adriamycin) of the thus obtained PEG-P(Asp.)ADR was mixed with a solution which has been prepared by dissolving 564.0 mg of adriamycin hydrochloride in 60 ml of DMF and adding 176 μl of triethylamine thereto, and the mixture was stirred at room temperature for 2 hours in the dark. After dialysis using a dialysis membrane (molecular weight cutoff=12,000~14,000), the resulting solution was freeze-dried. This was purified and concentrated by redissolving it in water and carrying out ultrafiltration using an ultrafiltration membrane of ADVANTEC UK-50 (molecular weight cutoff=50,000). This was further filtered using a 0.45 μ filter to obtain 59.4 ml of an aqueous solution of a block copolymer-drug complex pharmaceutical preparation. The thus obtained aqueous solution was found to have the HPLC chromatogram shown in FIG. 20. In the drawing, the peak ① is adriamycin, the peak ② is the dimer of adriamycin and the broad peak ③ is adriamycin linked to the polymer. The concentration of adriamycin (peak ①) was 1.10 mg/ml, and the concentration of the adriamycin dimer (peak ②) was 3.07 mg/ml. The weight ratio of adriamycin to the adriamycin dimer was 1:2.79. The measuring conditions of HPLC are as described in Example 3.

Example 9

Figure 21:
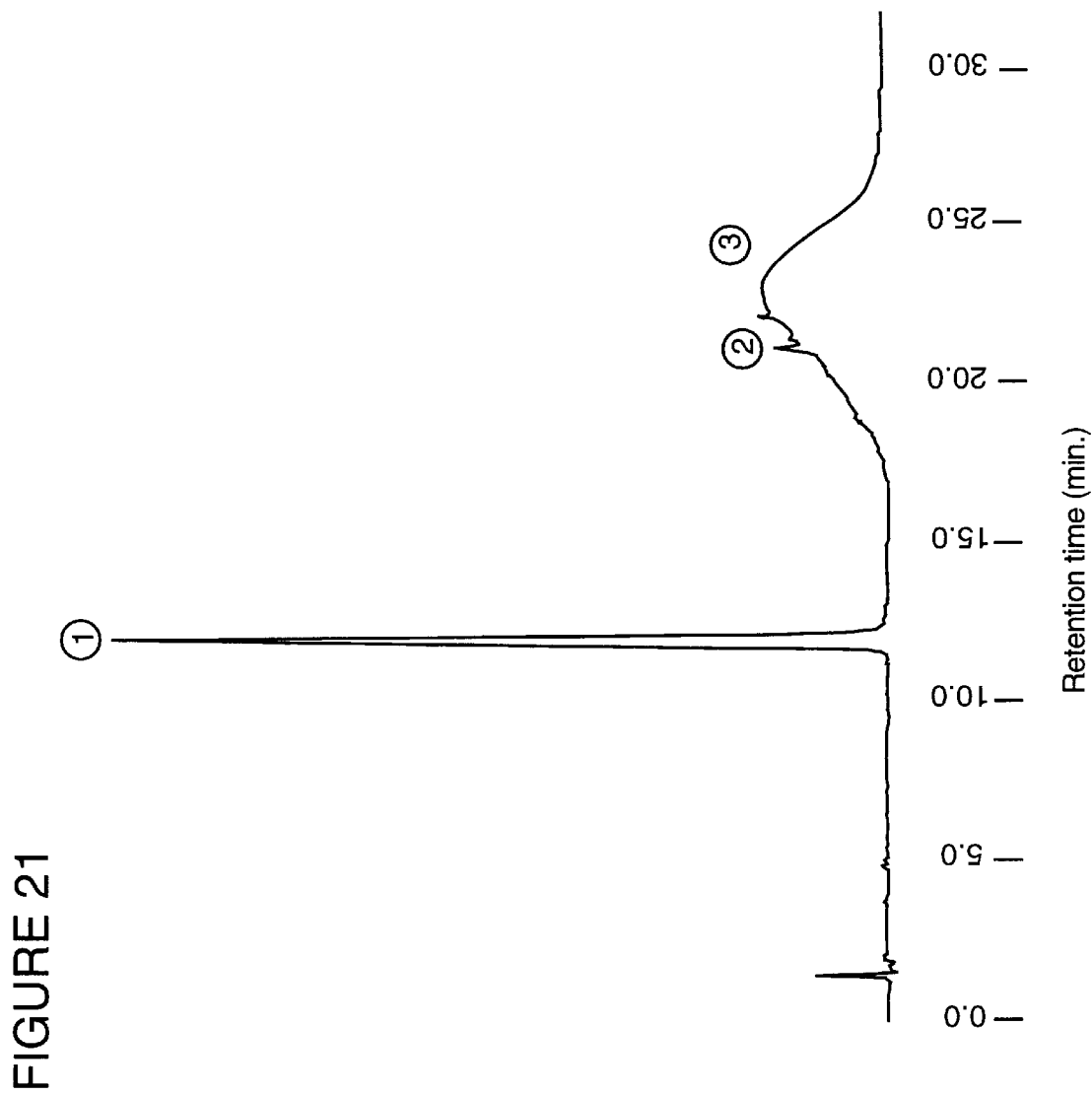
FIG. 21 shows a graph of HPLC chromatogram of the pharmaceutical preparation obtained from Example 9.

A 10 ml portion of the aqueous solution containing 12 mg/ml (as adriamycin) of the PEG-P(Asp.)ADR prepared in Example 8 was mixed with a solution which has been prepared by dissolving 32.0 mg of adriamycin hydrochloride in 30 ml of DMF and adding 10.0 μl of triethylamine thereto, and the mixture was stirred at room temperature for 2 hours in the dark. After dialysis using a dialysis membrane (molecular weight cutoff=12,000~14,000), the resulting solution was freeze-dried. This was redissolved in water and purified and concentrated by carrying out ultrafiltration using an ultrafiltration membrane of ADVANTEC UK-50 (molecular weight cutoff=50,000). This was further filtered using a 0.45 μ filter to obtain 9.1 ml of an aqueous solution of a block copolymer-drug complex pharmaceutical preparation. The thus obtained aqueous solution was found to have the HPLC chromatogram shown in FIG. 21. In the drawing, the peak ① is adriamycin, the peak ② is the dimer of adriamycin and the broad peak ③ is adriamycin linked to the polymer. The concentration of adriamycin (peak ①) was 1.98 mg/ml, and the concentration of the adriamycin dimer (peak ②) was 0.12 mg/ml. The weight ratio of adriamycin to the adriamycin dimer was 1:0.06. The measuring conditions of HPLC are as described in Example 3.

Example 10

Figure 22:
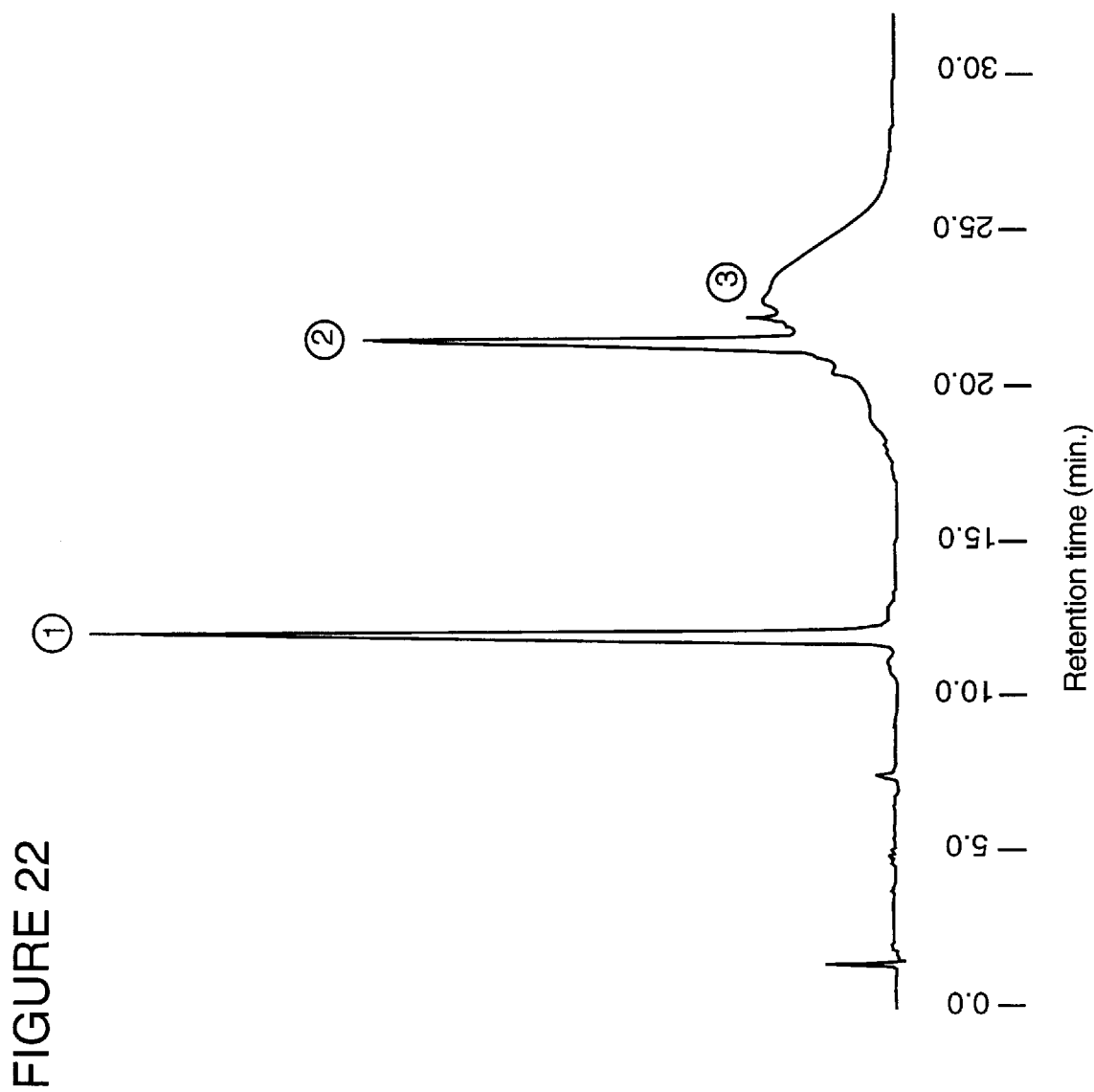
FIG. 22 shows a graph of HPLC chromatogram of the pharmaceutical preparation obtained from Example 10.

A 5 ml portion of the aqueous solution containing 12 mg/ml (as adriamycin) of the PEG-P(Asp.)ADR prepared in Example 8 was mixed with a solution which has been prepared by dissolving 51.4 mg of adriamycin hydrochloride in 15 ml of DMF and adding 16.0 μl of triethylamine thereto, and the mixture was stirred at room temperature for 2 hours in the dark. After dialysis using a dialysis membrane (molecular weight cutoff=12,000~14,000), the resulting solution was freeze-dried. This was redissolved in water and purified and concentrated by carrying out ultrafiltration using an ultrafiltration membrane of ADVANTEC UK-50 (molecular weight cutoff=50,000). This was further filtered using a 0.45 μ filter to obtain 15.2 ml of an aqueous solution of a block copolymer-drug complex pharmaceutical preparation. The thus obtained aqueous solution was found to have the HPLC chromatogram shown in FIG. 22. In the drawing, the peak ① is adriamycin, the peak ② is the dimer of adriamycin and the broad peak ③ is adriamycin linked to the polymer. The concentration of adriamycin (peak ①) was 1.04 mg/ml, and the concentration of the adriamycin dimer (peak ②) was 0.88 mg/ml. The weight ratio of adriamycin to the adriamycin dimer was 1:0.85. The measuring conditions of HPLC are as described in Example 3.

Example 11

Figure 23:
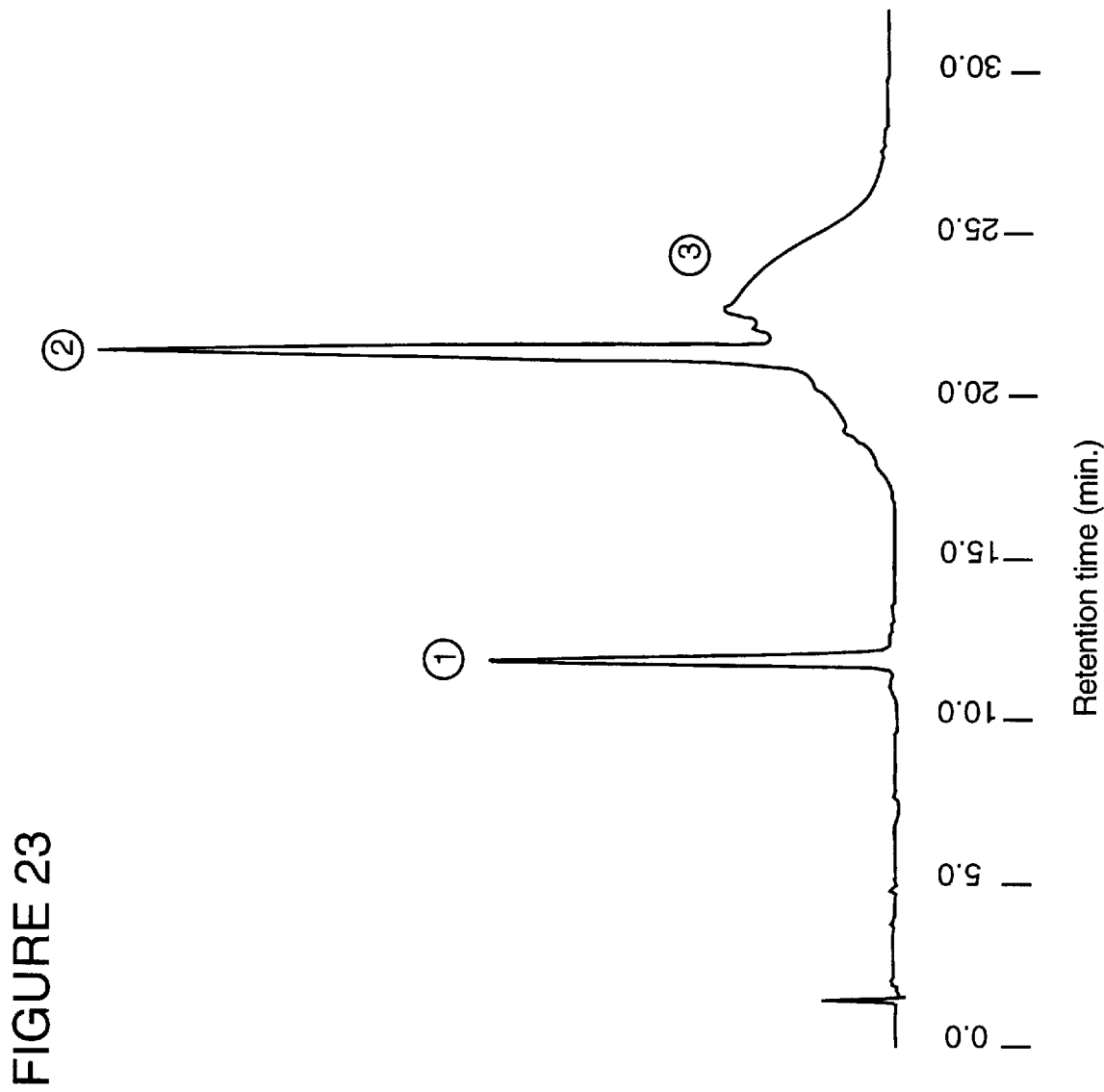
FIG. 23 shows a graph of HPLC chromatogram of the pharmaceutical preparation obtained from Example 11.

A solution which has been prepared by dissolving 103.5 mg of the adriamycin dimer prepared in Example 1 (2) and 49.1 mg of adriamycin hydrochloride in 65 ml of DMF was mixed with 23 ml of the aqueous solution containing 12 mg/ml (as adriamycin) of the PEG-P(Asp.)ADR prepared in Example 8, and the mixture was stirred at room temperature for 2 hours in the dark. After dialysis using a dialysis membrane (molecular weight cutoff=12,000~14,000), the resulting solution was purified and concentrated by carrying out ultrafiltration using an ultrafiltration membrane of ADVANTEC UK-50 (molecular weight cutoff=50,000). This was further filtered using a 0.45 μ filter to obtain 14.9 ml of an aqueous solution of a block copolymer-drug complex pharmaceutical preparation. The thus obtained aqueous solution was found to have the HPLC chromatogram shown in FIG. 23. In the drawing, the peak ① is adriamycin, the peak ② is the dimer of adriamycin and the broad peak ③ is adriamycin linked to the polymer. The concentration of adriamycin (peak ①) was 1.13 mg/ml, and the concentration of the adriamycin dimer (peak ②) was 2.76 mg/ml. The weight ratio of adriamycin to the adriamycin dimer was 1:2.44. The measuring conditions of HPLC are as described in Example 3.

Example 12

Figure 24:
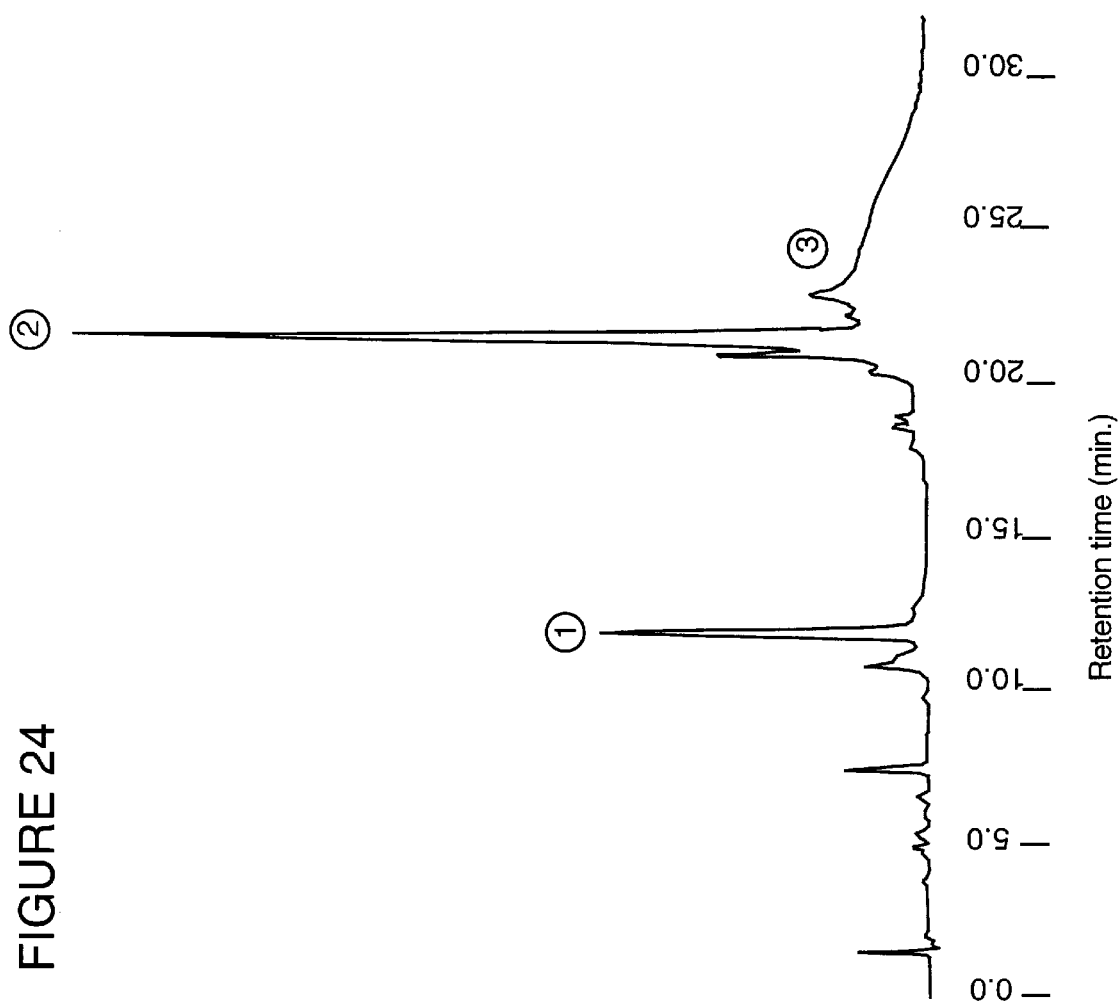
FIG. 24 shows a graph of HPLC chromatogram of the pharmaceutical preparation obtained from Example 12.

A 1.0034 g portion of the PEG-P(Asp.) prepared in Example 8 was dissolved in 16.7 ml of DMF to which was subsequently added 16.7 ml of acetonitrile. This was added with 1.7504 g of dicyclohexyl-carbodiimide (DCC), stirred for 5 minutes and then mixed with a solution which has been prepared by dissolving 474.4 mg of daunomycin hydrochloride in 33.3 ml of DMF and adding 152 μl of triethylamine thereto, and the mixture was allowed to reacted for 4 hours at room temperature. After the reaction, this was added with 3.3 ml of an aqueous 0.5% phosphoric acid solution and stirred for 5 minutes. After its dialysis using a dialysis membrane (molecular weight cutoff=12,000~14,000), the precipitate originated from DCC was removed by filtration. The resulting filtrate was concentrated by carrying out ultrafiltration using an ultrafiltration membrane of ADVANTEC UK-50 (molecular weight cutoff=50,000) to obtain 36 ml of an aqueous solution having a concentration of 12 mg/ml as daunomycin (calculated from its absorbance at 485 nm measured by an ultraviolet ray spectrophotometer). The thus obtained PEG-P(Asp.)DAM has the structure of the aforementioned formula (2) in which $R_1$ is a methyl group, $R_2$ is a trimethylene group, $R_3$ is a methyl group, a portion of $R_4$ is a hydroxyl group and the rest thereof is the aforementioned residue of formula (3) [Y is $CH_3$, Z is H], $R_5$ is hydrogen, n=350, m=32 and x=8. The daunomycin content was 30.3%, and it showed appropriate water solubility. A 7 ml portion of the aqueous solution containing 12 mg/ml (as daunomycin) of the thus obtained PEG-P(Asp.)DAM was mixed with a solution which has been prepared by dissolving 179.8 mg of adriamycin hydrochloride in 21 ml of DMF and adding 55.9 μl of triethylamine thereto, and the mixture was stirred at room temperature for 2 hours in the dark. After dialysis using a dialysis membrane (molecular weight cutoff=12,000~14,000), the resulting solution was freeze-dried. This was redissolved in water, purified and concentrated by carrying out ultrafiltration using an ultrafiltration membrane of ADVANTEC UK-50 (molecular weight cutoff=50,000) and then further filtered using a 0.45 μ filter to obtain 16.5 ml of an aqueous solution of a block copolymer-drug complex pharmaceutical preparation. The thus obtained aqueous solution was found to have the HPLC chromatogram shown in FIG. 24. In the drawing, the peak ① is adriamycin, the peak ② is the dimer of adriamycin and the broad peak ③ is daunomycin linked to the polymer. The concentration of adriamycin (peak ①) was 1.07 mg/ml, and the concentration of the adriamycin dimer (peak ②) was 3.26 mg/ml. The weight ratio of adriamycin to the adriamycin dimer was 1:3.05. The measuring conditions of HPLC are as described in Example 3.

Application Example 2

Colon 26 adenocarcinoma cells were transplanted subcutaneously in the subaxillary region of each CDF1 female mouse, to which the block copolymer-drug complex pharmaceutical preparation prepared in Example 6 or 7 or $^{14}$C-labeled adriamycin hydrochloride was intravenously administered 12 days after transplanting. Each drug was used by diluting it in physiological saline prior to its use. After 15 minutes and 1, 4, 24 and 48 hours of the administration, blood samples were collected and various organs were excised. The drug concentrations in the blood plasma and each internal organ were determined by measuring radioactivity thereof using a liquid scintillation counter. In this test, both adriamycin and adriamycin dimer are labeled with $^{14}$C. Periodical variations in the total amount (% of dose/ml) of adriamycin and adriamycin dimer in 1 ml of the blood plasma when the total amount of adriamycin and adriamycin dimer in the administered drug preparation is defined as 100 are shown in Table 3. While the drug quickly disappeared from blood plasma after its administration when adriamycin hydrochloride alone was administered, the drug remained in blood plasma at a higher level for a prolonged period of time in the case of the pharmaceutical preparation of the present invention. Improvement of the drug-retentivity was particularly significant in the case of the pharmaceutical preparation of Example 6 comprising the adriamycin dimer at a higher level. Periodical variations in the total amount (% of dose/g) of adriamycin and adriamycin diner in 1 g of the tumor tissue when the total amount of adriamycin and adriamycin dimer in the administered drug preparation is defined as 100 are shown in Table 4. Also, periodical variations in said total amount (% of dose/g) in the heart are shown in Table 5. In comparison with the case of the single administration of adriamycin hydrochloride, the drug administered as the pharmaceutical preparation of the present invention was slightly lower in its initial concentration and decreased in the course of time in the heart, but was accumulated in a several times higher concentration and increased in the course of time in the tumor portion. The drug-accumulation in tumor was particularly significant in the case of the pharmaceutical preparation of Example 6 comprising the adriamycin dimer at a higher level.

Application Example 3

Figure 25:
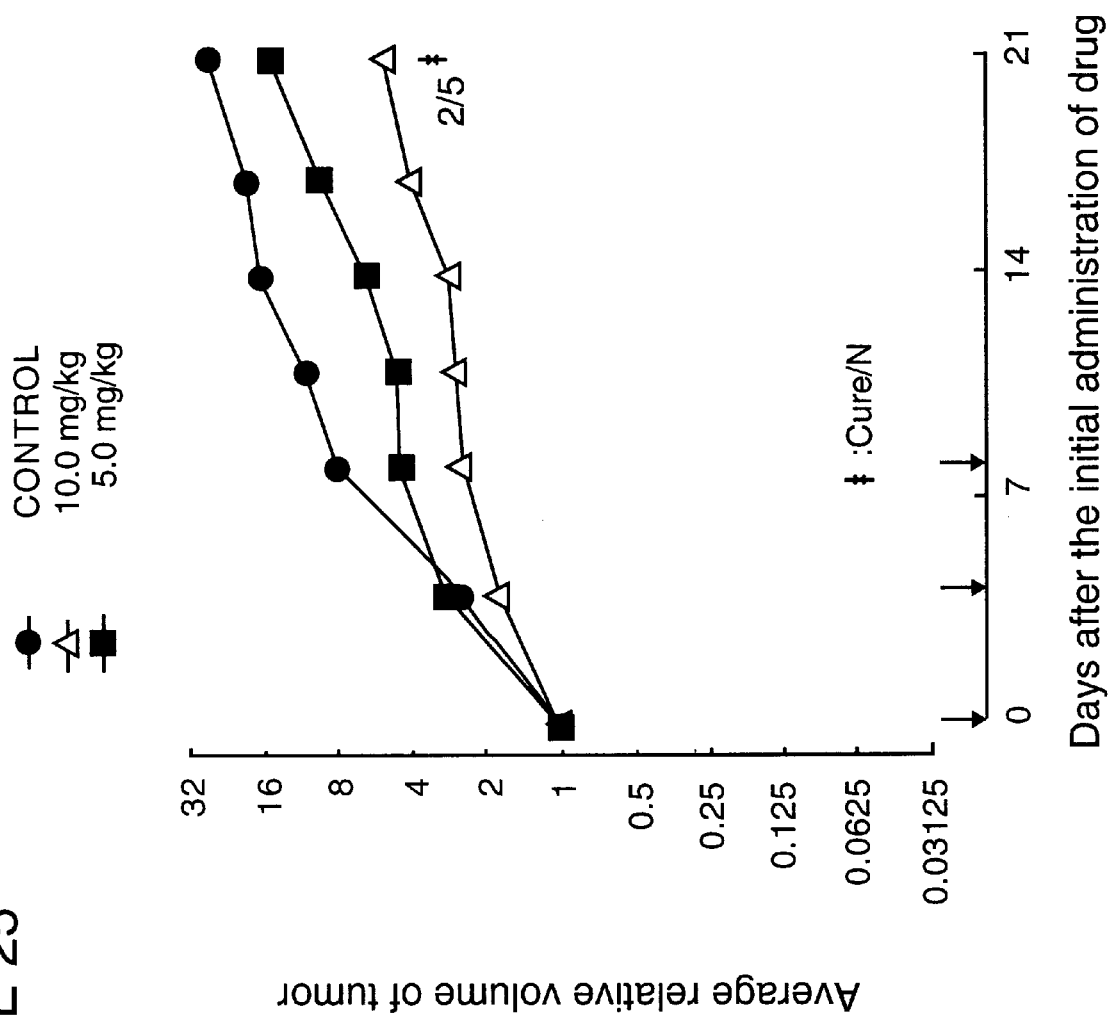
FIGS. 25, 26 or 27 shows a graph of tumor growth curve of mouse Colon 26 adenocarcinoma when the mouse was administered with adriamycin hydrochloride, the pharmaceutical preparation from Example 8 or the pharmaceutical preparation from Example 12 respectively in Application Example 3.
Figure 26:
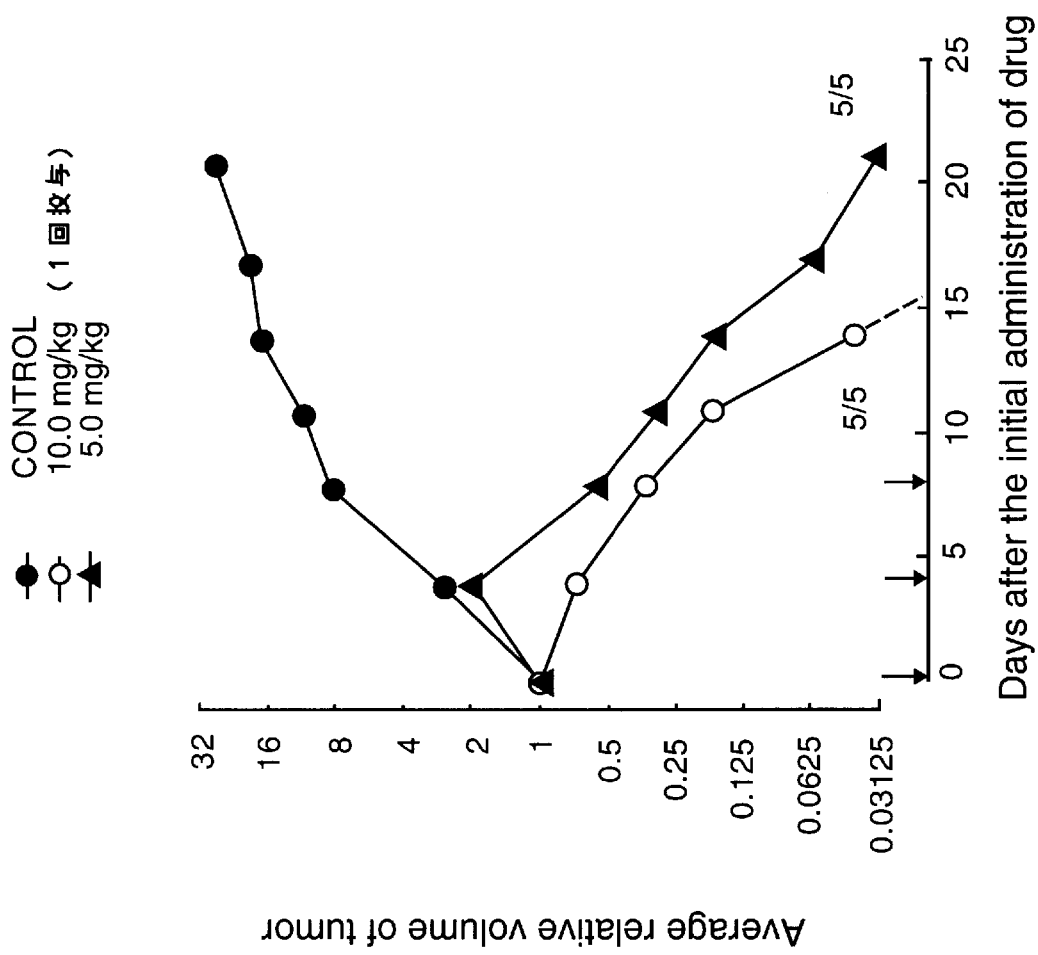
Figure 27:
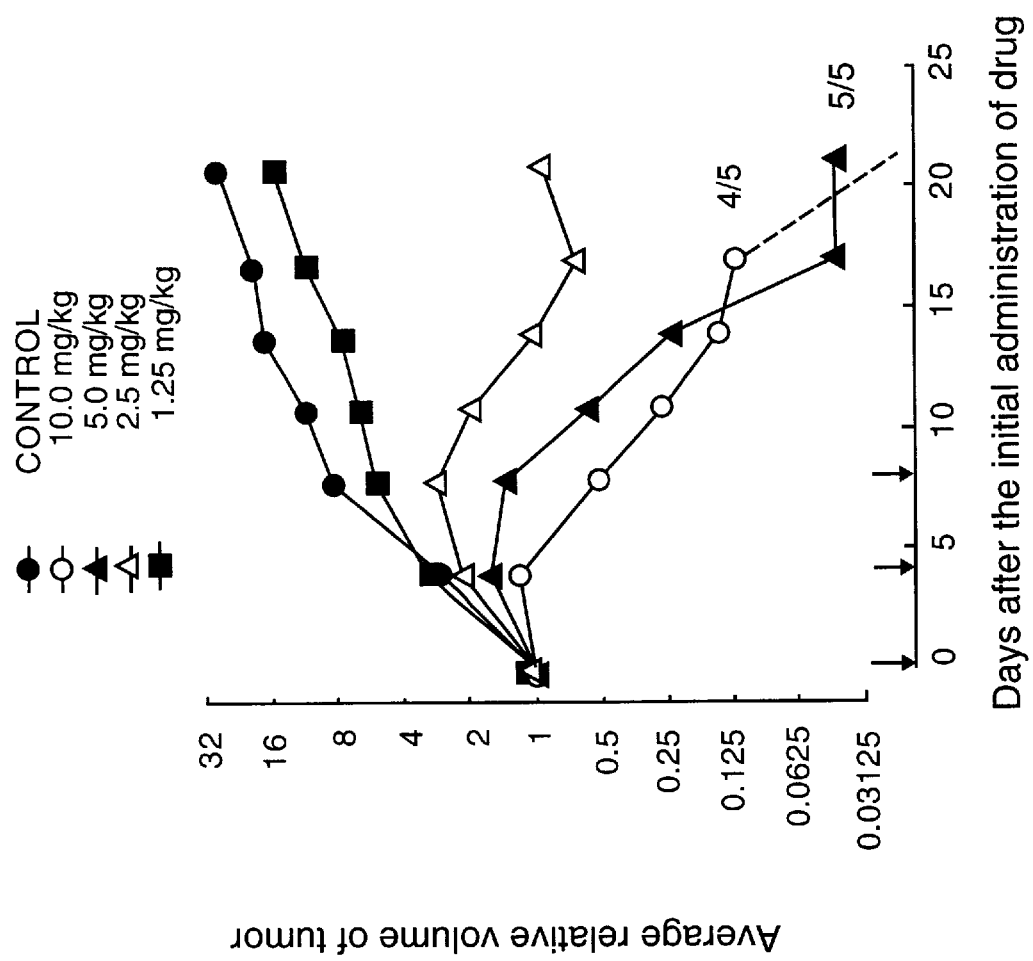

Colon 26 adenocarcinoma cells were transplanted subcutaneously in the subaxillary region of each CDF1 female mouse. When volume of the tumor reached around 100 mm$^3$, the block copolymer-drug complex pharmaceutical preparation prepared in Example 8 or 12 or adriamycin hydrochloride was intravenously administered once a day every 4th day in total of three times (indicated by arrows in the drawings) to examine their antitumor effects. In the case of the pharmaceutical preparation of Example 8, its effect obtained from the only first administration was also examined. Each drug was used by diluting it in physiological saline prior to its use. Each dose was determined as the amount of adriamycin of the peak ① of the HPLC chromatogram. The antitumor effects of each drug were estimated based on the tumor growth curve and the number of mice in which the tumor disappeared. The results are shown in Table 6 and FIGS. 25, 26 and 27. In comparison with the case of the administration of adriamycin hydrochloride, larger number of tumor-disappeared mice was observed with broader range of dose when the pharmaceutical preparation of Example 8 or 12 was administered.

Application Example 4

Colon 26 adenocarcinoma cells were transplanted subcutaneously in the subaxillary region of each CDF1 female mouse, to which the block copolymer-drug complex pharmaceutical preparation prepared in Example 8 or 9 was intravenously administered 8 days after transplanting. Each drug was used by diluting it in physiological saline prior to its use. After 15 minutes and 1, 4, 24 and 48 hours of the administration, blood samples were collected and various organs were excised. The concentrations of adriamycin and adriamycin dimer in the blood plasma and the tumor were determined by extracting the drugs with an organic solvent and measuring them by HPLC. Periodical variations in the amount (% of dose/ml) of adriamycin in 1 ml of the blood plasma when the amount of adriamycin in the administered drug preparation is defined as 100, and periodical variations in the amount (% of dose/ml) of adriamycin dimer in 1 ml of the blood plasma when the amount of adriamycin dimer in the administered drug preparation is defined as 100 are shown in Table 7. Improvement of the drug-retentivity in blood was particularly significant in the case of the pharmaceutical preparation of Example 8 comprising the adriamycin dimer at a higher level. Periodical variations in the amount (% of dose/g) of adriamycin in 1 g of the tumor tissue when the amount of adriamycin in the administered drug preparation is defined as 100, and periodical variations in the amount (% of dose/g) of adriamycin dimer in 1 g of the tumor tissue when the amount of adriamycin dimer in the administered drug preparation is defined as 100 are shown in Table 8. The drug-accumulation in tumor was markedly improved in the case of the pharmaceutical preparation of Example 8 comprising the adriamycin dimer at a higher level.

Application Example 5

Colon 26 adenocarcinoma cells were transplanted subcutaneously in the subaxillary region of each CDF1 female mouse, to which the block copolymer-drug complex pharmaceutical preparation prepared in Example 8, 10 or 12 was intravenously administered 11 days after transplanting. Each drug was used by diluting it in physiological saline prior to its use. After 1 or 24 hours of the administration, blood samples were collected and various organs were excised. The concentrations of adriamycin and adriamycin dimer in the blood plasma and the tumor were determined by extracting the drugs with an organic solvent and measuring them by HPLC. Periodical variations in the amount (% of dose/ml) of adriamycin in 1 ml of the blood plasma when the amount of adriamycin in the administered drug preparation is defined as 100, and periodical variations in the amount (% of dose/ml) of adriamycin dimer in 1 ml of the blood plasma when the amount of adriamycin dimer in the administered drug preparation is defined as 100 are shown in Table 9. Results of the pharmaceutical preparation of Example 8 were almost the same as those obtained from Application Example 4. The drug-retentivity in blood was slightly lower in the case of the pharmaceutical preparation of Example 10 in which the ratio of the adriamycin dimer was lower than that of the pharmaceutical preparation of Example 8. Periodical variations in the amount (% of dose/g) of adriamycin in 1 g of the tumor tissue when the amount of adriamycin in the administered drug preparation is defined as 100, and periodical variations in the amount (% of dose/g) of adriamycin dimer in 1 g of the tumor tissue when the amount of adriamycin dimer in the administered drug preparation is defined as 100 are shown in Table 10. With regard to the pharmaceutical preparation of Example 8, almost the same results as those obtained from Application Example 4 were obtained. The drug-accumulation in tumor was also slightly lower in the case of the pharmaceutical preparation of Example 10 in which the ratio of the adriamycin dimer was lower than that of the pharmaceutical preparation of Example 8.

TABLE 3

Periodical variations in % of dose/ml (blood plasma)

| Sample | Time after administration | | | | |
|---|---|---|---|---|---|
| | 15 minutes | 1 hour | 4 hours | 24 hours | 48 hours |
| (A) | 0.47 | 0.29 | 0.36 | 0.10 | 0.07 |
| (B) | 61.6 | 53.7 | 39.2 | 15.9 | 4.7 |
| (C) | 41.7 | 29.2 | 21.3 | 8.2 | 2.2 |

(A) Adriamycin hydrochloride
(B) Pharmaceutical preparation of Example 6
(C) Pharmaceutical preparation of Example 7

TABLE 4

Periodical variations in % of dose/g (tumor)

| Sample | Time after administration | | | | |
|---|---|---|---|---|---|
| | 15 minutes | 1 hour | 4 hours | 24 hours | 48 hours |
| (A) | 2.3 | 2.4 | 1.7 | 1.3 | 1.0 |
| (B) | 2.3 | 3.8 | 4.9 | 9.6 | 9.1 |
| (C) | 2.3 | 2.7 | 4.9 | 7.0 | 4.0 |

(A) Adriamycin hydrochloride
(B) Pharmaceutical preparation of Example 6
(C) Pharmaceutical preparation of Example 7

TABLE 5

Periodical variations in % of dose/g (heart)

| Sample | Time after administration | | | | |
|---|---|---|---|---|---|
| | 15 minutes | 1 hour | 4 hours | 24 hours | 48 hours |
| (A) | 10.5 | 7.0 | 4.6 | 1.1 | 0.5 |
| (B) | 4.9 | 4.2 | 3.3 | 1.6 | 1.0 |
| (C) | 6.5 | 5.4 | 3.8 | 1.4 | 0.7 |

(A) Adriamycin hydrochloride
(B) Pharmaceutical preparation of Example 6
(C) Pharmaceutical preparation of Example 7

TABLE 6

Antitumor activity on mouse Colon 26 adenocarcinoma

| Sample | Dose (mg/kg) | Tumor-disappeared mice |
|---|---|---|
| Adriamycin hydrochloride | 5 | 0/5 |
| | 10 | 2/5 |
| Pharmaceutical preparation of Example 8 | 5 | 5/5 |
| | 10* | 5/5 |
| Pharmaceutical preparation of Example 12 | 1.25 | 0/5 |
| | 2.5 | 0/5 |
| | 5 | 4/5 |
| | 10 | 5/5 |

(* first administration only)

TABLE 7

Periodical variations in % of dose/ml (blood plasma)

| Sample | | Time after administration | | | | |
|---|---|---|---|---|---|---|
| | | 15 minutes | 1 hour | 4 hours | 24 hours | 48 hours |
| (A) | ① | 44.9 | 32.9 | 20.7 | 3.8 | 2.0 |
| | ② | 67.2 | 69.7 | 61.9 | 14.2 | 3.9 |
| (B) | ① | 27.7 | 12.3 | 5.3 | 1.9 | 0.5 |
| | ② | 23.0 | 22.5 | 19.4 | 11.1 | 7.0 |

(A) Pharmaceutical preparation of Example 8
(B) Pharmaceutical preparation of Example 9
① Adriamycin
② Adriamycin dimer

TABLE 8

Periodical variations in % of dose/g (tumor)

| Sample | | Time after administration | | | | |
|---|---|---|---|---|---|---|
| | | 15 minutes | 1 hour | 4 hours | 24 hours | 48 hours |
| (A) | ① | 4.0 | 3.1 | 6.8 | 19.0 | 20.4 |
| | ② | 1.1 | 1.0 | 6.4 | 14.1 | 12.2 |
| (B) | ① | 1.3 | 2.1 | 1.9 | 2.2 | 1.2 |
| | ② | 0.0 | 8.1 | 2.8 | 3.9 | 4.9 |

(A) Pharmaceutical preparation of Example 8
(B) Pharmaceutical preparation of Example 9
① Adriamycin
② Adriamycin dimer

TABLE 9

Periodical variations in % of dose/ml (blood plasma)

| Sample | | Time after administration | |
|---|---|---|---|
| | | 1 hour | 24 hours |
| (A) | ① | 36.7 | 6.8 |
| | ② | 83.5 | 17.9 |
| (B) | ① | 11.0 | 4.1 |
| | ② | 65.3 | 16.2 |
| (C) | ① | 40.6 | 10.2 |
| | ② | 100.2 | 24.5 |

(A) Pharmaceutical preparation of Example 8
(B) Pharmaceutical preparation of Example 10
(C) Pharmaceutical preparation of Example 12
① Adriamycin
② Adriamycin dimer

TABLE 10

| Sample | Periodical variations in % of dose/g (tumor) | |
|---|---|---|
| | Time after administration | |
| | 1 hour | 24 hours |
| (A) ① | 3.4 | 21.0 |
| ② | 1.8 | 16.1 |
| (B) ① | 2.6 | 4.5 |
| ② | 0.1 | 3.0 |
| (C) ① | 5.0 | 9.1 |
| ② | 2.1 | 6.3 |

(A) Pharmaceutical preparation of Example 8
(B) Pharmaceutical preparation of Example 10
(C) Pharmaceutical preparation of Example 12
① Adriamycin
② Adriamycin dimer

EFFECTS OF THE INVENTION

It was successful to endow the dimer-, trimer- or tetramer-containing high molecular block copolymer-drug complex pharmaceutical preparation of the present invention with higher drug effects and lower toxicity by incorporating anticancer agents and the like into the inner core of micelle of the block copolymer. In consequence, the present invention can provide markedly useful pharmaceutical preparations.

What is claimed is:

1. A dimer, trimer or tetramer of anthracycline compound which is obtained by directly chemically bonding anthracycline compound or compounds having anticancer activities to each other by an alkali treatment.

2. The dimer, trimer or tetramer of anthracycline compound according to claim 1 wherein the anthracycline compound or compounds are selected from the croup consisting of adriamycin, daunomycin, pirarubicin, epirubicin and acid salts thereof.

3. The dimer of anthracycline compound which is obtained by directly chemically bonding adriamycin molecules or acid salts thereof to each other, or by directly chemically bonding adriamycin or an acid salt thereof to daunomycin or an acid salt thereof, by an alkali treatment.

4. The dimer, trimer or tetramer of anthracycline compound according to claim 1 or 2, or the dimer of anthracycline compound according to claim 3, wherein the mutual binding mode of anthracycline compounds is Schiff base bonding.

5. A dimer of adriamycin having the structure of the following formula (AA):

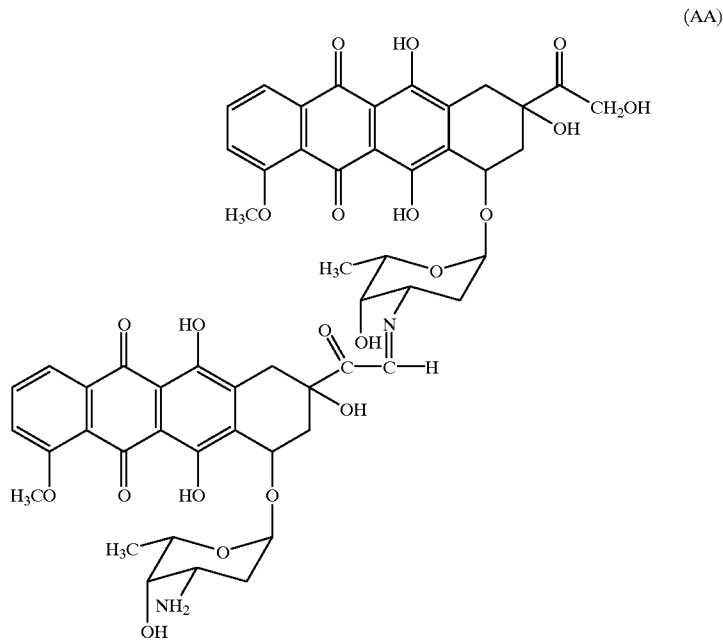

6. A trimer of adriamycin which is obtained by directly, chemically bonding adriamycin molecules or acid salts thereof to each other by an alkali treatment and has the mass spectrum shown in FIG. 7.

7. A high molecular block copolymer-drug complex pharmaceutical preparation in which the high molecular block copolymer having a hydrophilic polymer segment and a hydrophobic polymer segment forms a micelle having the hydrophilic segment as its outer shell and contains in its hydrophobic inner core a dimer, trimer or tetramer of anthracycline compound which is obtained by directly chemically bonding anthracycline compound or compounds having anticancer activities to each other by an alkali treatment, optionally with one or more other drugs.

8. The high molecular block copolymer-drug complex pharmaceutical preparation in which the high molecular block copolymer having a hydrophilic polymer segment and a hydrophobic polymer segment forms a micelle having the hydrophilic segment as its outer shell and contains in its hydrophobic inner core a dimer, trimer or tetramer of anthracycline compound, optionally with one or more other drugs wherein the dimer, trimer or tetramer of anthracycline compound is the dimer, trimer or tetramer of anthracycline compound of claim 1, 2, 3, 5 or 6.

9. The high molecular block copolymer-drug complex pharmaceutical preparation according to claim 7 wherein the high molecular block copolymer has a structure of the following formula (1) or (2):

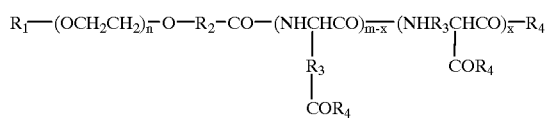

(1)

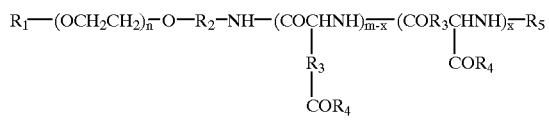

(2)

wherein $R_1$ represents a hydrogen atom or a lower alkyl group, $R_2$ represents a binding group, $R_3$ represents a methylene or ethylene group, $R_4$ independently represents a hydroxyl group or a residue of an anthracycline compound having anticancer activity, $R_5$ represents a hydrogen atom or a protecting group, n is an integer of 5 to 1,000, m is an integer of 2 to 300 and x is an integer of 0 to 300, with the proviso that x is not larger than m.

10. The high molecular block copolymer-drug complex pharmaceutical preparation according to claim 9 wherein the residue of the anthracycline compound having anticancer activity is a group represented by the following formula (3):

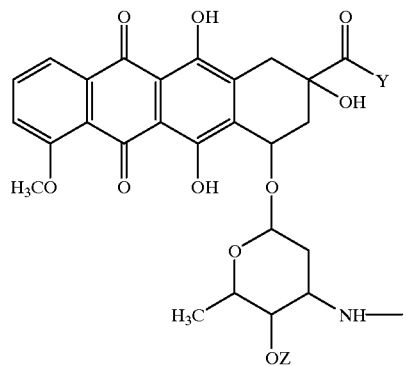

(3)

wherein Y represents —$CH_2OH$ or —$CH_3$ and Z represents H or

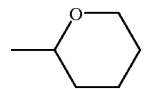

11. The high molecular block copolymer-drug complex pharmaceutical preparation according to claim 7, 9 or 10 wherein it contains in the inner core of micelle formed by the high molecular block copolymer said dimer, trimer or tetramer of anthracycline compound in an amount of from 2 to 60% by weight based on the high molecular block copolymer.

12. The high molecular block copolymer-drug complex pharmaceutical preparation according to claim 7, 9 or 10 wherein the dimer, trimer or tetramer of anthracycline compound is the dimer of adriamycin which is obtained by directly chemically bonding adriamycin molecules or acid salts thereof to each other by an alkali treatment.

13. The high molecular block copolymer-drug complex pharmaceutical preparation according to claim 7, 9 or 10 wherein said one or more other drugs is an anthracycline anticancer agent, and wherein the pharmaceutical preparation contains in the inner core of micelle formed by the high molecular block copolymer said anthracycline anticancer agent and said dimer, trimer or tetramer of anthracycline compound at the ratio of 1:0.5~20 by weight.

14. The high molecular block copolymer-drug complex pharmaceutical preparation according to claim 13, wherein said anthracycline anticancer agent and said dimer, trimer or tetramer of anthracycline compound are contained at the ratio of 1:0.7~10 by weight.

15. The high molecular block copolymer-drug complex pharmaceutical preparation according to claim 13 wherein said anthracycline anticancer agent and said dimer, trimer or tetramer of anthracycline compound are contained at the ratio of 1:1~5 by weight.

16. The high molecular block copolymer-drug complex pharmaceutical preparation according to claim 13, wherein said anthracycline anticancer agent is at least one agent selected from the group consisting of adriamycin, daunomycin, pirarubicin, epirubicin and acid salts thereof.

* * * * *